US010351492B2

(12) United States Patent
Pappo et al.

(10) Patent No.: US 10,351,492 B2
(45) Date of Patent: Jul. 16, 2019

(54) INTRODUCTION OF ALKYL SUBSTITUENTS TO AROMATIC COMPOUNDS

(71) Applicant: B. G. NEGEV TECHNOLOGIES AND APPLICATIONS LTD., AT BEN-GURION UNIVERSITY, Beer Sheva (IL)

(72) Inventors: Doron Pappo, Lehavim (IL); Regev Parnes, Beer Sheva (IL)

(73) Assignee: B. G. NEGEV TECHNOLOGIES AND APPLICATIONS, Beer Sheva (IL)

( * ) Notice: Subject to any disclaimer, the term of this patent is extended or adjusted under 35 U.S.C. 154(b) by 0 days.

(21) Appl. No.: 15/551,394

(22) PCT Filed: Feb. 16, 2016

(86) PCT No.: PCT/IL2016/050182
§ 371 (c)(1),
(2) Date: Aug. 16, 2017

(87) PCT Pub. No.: WO2016/132355
PCT Pub. Date: Aug. 25, 2016

(65) Prior Publication Data
US 2018/0065904 A1 Mar. 8, 2018

Related U.S. Application Data

(60) Provisional application No. 62/116,595, filed on Feb. 16, 2015.

(51) Int. Cl.
| C07C 15/04 | (2006.01) |
| C07C 319/18 | (2006.01) |
| C07C 321/20 | (2006.01) |
| C07B 31/00 | (2006.01) |
| C07B 37/04 | (2006.01) |
| C07B 45/06 | (2006.01) |
| A61K 31/015 | (2006.01) |
| A61K 31/10 | (2006.01) |
| A61K 31/335 | (2006.01) |
| A61K 31/565 | (2006.01) |
| C07C 317/14 | (2006.01) |
| C07C 327/06 | (2006.01) |
| C07C 253/30 | (2006.01) |
| C07C 39/14 | (2006.01) |
| C07C 39/38 | (2006.01) |
| C07C 43/225 | (2006.01) |
| C07C 43/23 | (2006.01) |
| C07J 1/00 | (2006.01) |
| C07J 31/00 | (2006.01) |
| C07D 317/64 | (2006.01) |
| C07D 209/10 | (2006.01) |
| A61K 31/47 | (2006.01) |
| C07C 323/16 | (2006.01) |
| C07C 323/56 | (2006.01) |
| C07C 323/60 | (2006.01) |
| C07C 319/14 | (2006.01) |
| C07C 323/63 | (2006.01) |

(52) U.S. Cl.
CPC ............ *C07C 15/04* (2013.01); *A61K 31/015* (2013.01); *A61K 31/10* (2013.01); *A61K 31/335* (2013.01); *A61K 31/47* (2013.01); *A61K 31/565* (2013.01); *C07B 31/00* (2013.01); *C07B 37/04* (2013.01); *C07B 45/06* (2013.01); *C07C 39/14* (2013.01); *C07C 39/38* (2013.01); *C07C 43/225* (2013.01); *C07C 43/23* (2013.01); *C07C 253/30* (2013.01); *C07C 317/14* (2013.01); *C07C 319/14* (2013.01); *C07C 319/18* (2013.01); *C07C 321/20* (2013.01); *C07C 323/16* (2013.01); *C07C 323/56* (2013.01); *C07C 323/60* (2013.01); *C07C 323/63* (2013.01); *C07C 327/06* (2013.01); *C07D 209/10* (2013.01); *C07D 317/64* (2013.01); *C07J 1/007* (2013.01); *C07J 31/006* (2013.01); *C07B 2200/05* (2013.01)

(58) Field of Classification Search
CPC ..... C07C 319/18; C07C 321/20; C07B 31/00; C07B 37/04; C07B 45/06; A61K 31/10; A61K 31/085; A61K 31/09; A61K 31/065
See application file for complete search history.

(56) References Cited

U.S. PATENT DOCUMENTS

| 5,661,159 A * | 8/1997 | Matsuo | C07D 405/04 514/314 |
| 2010/0099883 A1 * | 4/2010 | Fillers | C07D 333/12 546/280.4 |
| 2010/0190747 A1 * | 7/2010 | Suzuki | C07D 487/04 514/63 |

FOREIGN PATENT DOCUMENTS

| WO | 2008021369 A2 | 2/2008 | |
| WO | WO-2014033466 A1 * | 3/2014 | ............. C07K 1/122 |

OTHER PUBLICATIONS

Parnes et al. ("Thiol-Promoted Selective Addition of Ketones to Aldehydes", Organic Letters, vol. 16, Issue 22, Nov. 2014, pp. 5922-5925).*

(Continued)

Primary Examiner — Rosalynd A Keys
(74) Attorney, Agent, or Firm — The Roy Gross Law Firm, LLC; Roy Gross

(57) ABSTRACT

Novel selective synthesis route to introduce primary alkyl groups on aromatic compounds is disclosed. The synthesis route is based on electrophilic aromatic substitutions of thionium ion species that are generated in-situ from aldehydes and thiols, affording benzyl sulfide that can be reduced with triethylsilane.

8 Claims, 2 Drawing Sheets

(56) References Cited

OTHER PUBLICATIONS

Khan et al. (New three-component condensation reaction: synthesis of 1-[(alkylthio)(phenyl)methyl]-naphthalene-2-ol catalyzed by bromodimethylsulfonium bromide (BDMS), Tetrahedron Letters, vol. 52, Jul. 2011, pp. 5157-5160).*

Dar et al. ("Hydrated ferric sulfate catalyzed synthesis of 3-[(alkyl/arylthio)(aryl)methyl]-1H-indole derivatives through one-pot reaction", Tetrahedron Letters, vol. 55, 2014, pp. 486-489).*

Khorshidi et al. ("Sulfuric acid functionalized MCM-41 coated on magnetite nanoparticles as a recyclable core-shell solid acid catalyst for three-component condensation of indoles, aldehydes and thiols", RSC Adv., vol. 4, Aug. 2014, pp. 41469-41475.*

Wu et al. ("Hafnium Trifluoromethanesulfonate (Hafnium Triflate) as a Highly Efficient Catalyst for Chemoselective Thioacetalization and Transthioacetalization of Carbonyl Compounds", J. Org. Chem., vol. 73, No. 23, Nov. 2008, pp. 9522-9524).*

Kumar et al. (Multicomponent, solvent-free synthesis of β-aryl-β-mercapto ketones using zirconium chloride as a catalyst, Tetrahedron Letters, vol. 48, Issue 49, Dec. 2007, pp. 8730-8734).*

Oblasova et al. ("Toxicity of antiseptics of the phenol and naphthol series", Izvestiya Vysshikh Uchebnykh Zavedenii, Lesnoi Zhurnal (1973), 16(6), pp. 121-124).*

Tsuchimoto, T, et al., "Scandium(III) trifluoromethanesulfonate-catalysed reductive Friedel-Crafts benzylation of aromatic compounds using arenecarbaldehydes and propane-1,3-diol", Chemical Communications, Jan. 1, 1996, vol. 20, pp. 2345-2346.

Hatakeyama, Takuji et al, "Iron-Catalyzed Suzuki—Miyaura Coupling of Alkyl Halides", Journal of the American Chemical Society, Jul. 20, 2010, vol. 132, No. 31, pp. 10674-10676.

Gonzalez-Bobes, Francisco et al, "Amino Alcohols as Ligands for Nickel-Catalyzed Suzuki Reactions of Unactivated Alkyl Halides, Including Secondary Alkyl Chlorides, with Arylboronic Acids", Journal of the American Chemical Society, Apr. 1, 2006, vol. 128, No. 16, pp. 5360-5361.

Molander. Gary A. et al, "Nickel-Catalyzed Cross-Coupling of Potassium Aryl- and Heteroaryltrifluoroborates with Unactivated Alkyl Halides", Organic Letters, Nov. 19, 2010, vol. 12, No. 24, pp. 5783-5785.

Bair, Joseph S. et al, "Linear-Selective Hydroarylation of Unactivated Terminal and Internal Olefins with Trifluoromethyl-substitued Arenes", Journal of the American Chemical Society, Aug. 29, 2014, vol. 136, No. 38, pp. 13098-13101.

Parnes, R. et al., "Thiol-Promoted Selective Addition of Ketones to Aldehydes", Organic Letters, Nov. 21, 2014, vol. 16 No. 22, pp. 5922-5925.

Tamura, Y. et al., "Electrophilic aromatic substitution by pummerer reaction of alpha-sulfinylacetate" Tetrahedron Letters, Jan. 2, 1981, vol. 22 No. 1, pp. 81-84.

Khan, A. T. et al., "New three-component condensation reaction: synthesis of 1-[(alkylthio)(phenyl)methyl]-naphthalene-2-ol catalyzed by bromodimethylsulfonium bromide (BDMS)", Tetrahedron Letters, Jul. 31, 2011, vol. 52 No. 40, pp. 5157-5160.

Kenyon, J. et al., "968. Alkyl-oxygen fission in carboxylic esters. XI. Reactions of secondary alcohols containing the 2: 4: 6-trimethoxyphenyl radical", Journal of the Chemical Society, 1952, pp. 4964-4969.

Wu, Yan-Chao et al, "Hafuium Trifluoromethanesulfonate (Hafnium Triflate) as a Highly Efficient Catalyst for Chemoselective Thioacetalization and Transthioacetalization of Carbonyl Compounds", Journal of Organic Chemistry, Dec. 5, 2008, vol. 73 No. 23, pp. 9522-9524.

Kito, T. et al, "Alkylation of 2-naphthol by alcohols in the presence of base", Journal of Organic Chemistry, May 31, 1977, vol. 42 No. 11, pp. 2020-2021.

Amici, R. R. et al. "On Aromatic Electrophilic Substitution Promoted by In Situ Generated Thionium Ions" Synthesis, Feb. 27, 2013, vol. 45 No. 6, pp. 798-802.

Parnes, R. "Reductive Alkylation of Arenes by a Thiol-Based Multicomponent Reaction" Organic Letters, Jun. 2, 2015, vol. 17 No. 12, pp. 2924-2927.

Harikrishnan A. et al, "Friedel—Crafts hydroxyalkylation through activation of a carbonyl group using AlBr3: an easy access to pyridyl aryl/heteroaryl carbinols", New Journal of Chemistry, Dec. 2012, vol. 37 No. 3, pp. 563-567.

Chou C. et al, "A Convenient Preparation of Bis(4-methoxyphenyl)methanethiol and Its Application in the Synthesis of Biotin Thioacid", Journal of the Chinese Chemical Society, Mar. 2014, vol. 61 No. 6, pp. 707-710.

Hassanabadi A., "multicomponent synthesis of 1-[aryl (p-tolylsulfone)methyl]naphthalen-2-ols using p-toluenesulfonic acid as a catalyst", Journal of Chemical Research, Mar. 2013, vol. 37 No. 3, pp. 152-154.

Yoshinari Sawama et al, "Iron-Catalyzed Friedel—Crafts Benzylation with Benzyl TMS Ethers at Room Temperature", Chemistry: A European Journal, Jan. 2014, vol. 20 issue 2, pp. 510-516.

Teruhisa Tsuchimoto et al, "Scandium(III) trifluoromethanesulfonate-catalysed reductive Friedel—Crafts benzylation of aromatic compounds using arenecarbaldehydes and propane-1,3-diol", Chemical Communications, 1996, vol. 20, pp. 2345-2346.

Ken S. Feldman, "Modern Pummerer-type reactions", Tetrahedron, 2006, vol. 62, pp. 5003-5034.

Smith, L. H. S. et al, "Beyond the Pummerer Reaction: Recent Developments in Thionium Ion Chemistry", 2010, Angewandte Chemie International Edition, vol. 49 issue. 34, pp. 5832-5844.

Bur, S. K., "The Pummerer Reaction: Methodology and Strategy for the Synthesis of Heterocyclic Compounds", 2004, Chemical Reviews, vol. 104 issue 5, pp. 2401-2432.

Miller, M. et al, "Exploring a new, connective Pummerer reaction: formation of oxindoles by the reaction of thiols with glyoxamides", 2007, ChemComm, vol. 5, pp. 498-500.

Miller, M. et al, "Formation of N-heterocycles by the reaction of thiols with glyoxamides: exploring a connective Pummerer-type cyclisation", 2009, Organic and Biomolecular Chemistry, vol. 7 issue 3, pp. 589-597.

Ovens, C. et al, "Intramolecular aryl transfer to thionium ions in an approach to α-arylacetamides", 2009, ChemComm, vol. 21, pp. 3101-3103.

Kleiner, C. M. et al, "Hydrophobic amplification of noncovalent organocatalysis", 2006, Chemical Communications, vol. 41, pp. 4315-4317.

Stamos, I. K. et al, "Mild reaction of pummerer rearrangement products with aromatic compounds in the presence of lewis acids. Application to the preparation of arylmethylene ketones, arylacetoesters, and arylacetonitriles", 1985, Tetrahedron Letters, vol. 26 issue 4, pp. 477-480.

Tamura, Y. et al, "Acid-catalyzed cyclizations of n-vinyl-α-sulfinylacetamides A novel synthetic approach to erythrinane", 1982, Tetrahedron Letters, vol. 23 issue 21, pp. 2209-2212.

Tamura, Y. et al, "Facile Syntheses of Oxindoles and 3-Oxo-1,2,3,4-tetrahydroisoquinolines", Synthesis, 1981, vol. 07, pp. 534-537.

Jousse-Karinthi, C. et al, "Synthetic Application of Sequential Palladium-Catalyzed Allylic Acetate Alkylation and Michael Addition Carbocyclization: Synthesis of (±)-Dihydroerythramine", 2001, European Journal of Organic Chemistry, vol. 19, pp. 3631-3640.

Horiguchi, Y. et al, "A Synthesis of Heteroaromatic Analogues of 1-Methyl-1,2,3,4-tetrahydroisoquinoline Using the Pummerer-Type Cyclization Reaction: Observation of Tandem Cyclization Reaction", 2004, Chemical and Pharmaceutical Bulletin, vol. 52 issue 2, pp. 214-220.

Sommer, L. H. et al, "Stereochemistry of asymmetric silicon. XVII. Synthesis, resolution, and stereochemistry of the 1,2,2,2-tetraphenyl-1-methyldisilane system", 1969, Journal of the American Chemical Society, vol. 91 issue 25, pp. 7067-7076.

* cited by examiner

INTRODUCTION OF ALKYL SUBSTITUENTS TO AROMATIC COMPOUNDS

RELATED APPLICATIONS

This application is a National Phase of PCT Patent Application No. PCT/IL2016/050182 having International filing date of Feb. 16, 2016, which claims the benefit of priority from U.S. Patent Application No. 62/116,595, filed on Feb. 16, 2015. The contents of the above applications are all incorporated by reference as if fully set forth herein in their entirety.

FIELD OF THE INVENTION

The present invention, in some embodiments thereof, relates to a novel synthesis route of electrophilic aromatic substitution and, more particularly, but not exclusively, to introducing alkyl groups to aromatic compounds.

BACKGROUND OF THE INVENTION

Aromatic and heteroaromatic substructure are among the most important structural motifs abundant in organic molecules. The Friedel-Crafts alkylation [Olah, G. A. Friedel-crafts chemistry. Wiley New York: 1973], one of the oldest known chemical transformations, is the preferred method for introducing alkyl substituents, derived from alkyl halides, onto aromatic compounds [Rueping, M. et al. Org. Chem. 2010, 6, 6.]. Over the years, the classic methods have seen improvements and techniques that are less destructive, non-toxic and have higher selectivity [Mertins, K. et al, Angewandte Chemie International Edition 2005, 44, 238] were developed.

While this method is reliable for installation of benzyl groups and secondary and tertiary alkyl moieties [Sawama, Y. et al., Chemistry—A European Journal 2014, 20, 510], the major limitation of the reaction lies in the fact that it is unsuitable for primary alkyl halides. The latter react less readily, therefore require harsh conditions [Smith, M. B.; March, J., March's Advanced Organic Chemistry: Reactions, Mechanisms, and Structure. Wiley: 2007; Carey, F. A.; Sundberg, R. J., Advanced Organic Chemistry: Part A: Structure and Mechanisms. Springer: 2007], and result in a mixture of rearrangement products. Other major drawbacks, such as polyalkylation of the aromatic core, and the requirement for strict anhydrous conditions, further affect the applicability of the process. To overtake the synthetic difficulties of placing primary alkyl groups onto aromatic compounds, alternative multi-step protocols have been developed, such as Friedel-Crafts acylation and reduction, reductive Friedel-Crafts alkylation [suchimoto, T et al., Chemical Communications 1996, 2345], metal catalyzed cross-coupling [Hatakeyama, T. et al. J. Am. Chem. Soc. 2010, 132, 10674; González-Bobes, F., Fu, G. C. J. Am. Chem. Soc. 2006, 128, 5360; Molander, G. A. et al. Org. Lett. 2010, 12, 5783; Yang, C. T. et al., Angew. Chem. Int. Ed. 2011, 50, 3904. Li, C. et al, Angewandte Chemie International Edition 2015], and metal catalyzed C—H activation [Bair, J. S. et al., J. Am. Chem. Soc. 2014, 136, 13098; Robbins, D. W.; Hartwig, J. F. Angew. Chem. Int. Ed. 2013, 52, 933].

SUMMARY OF THE INVENTION

The present invention, in some embodiments thereof, relates to a novel synthesis route of electrophilic aromatic substitution and, more particularly, but not exclusively, to introducing alkyl groups to aromatic compounds.

According to an aspect of some embodiments of the present invention, there is provided a process for synthesis of a compound represented by Formula I:

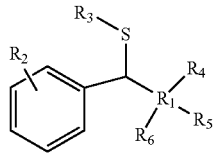

Formula I the process comprising:
reacting a compound represented by Formula II:

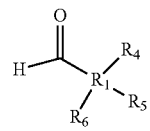

Formula II with a compound represented by Formula III:

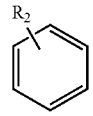

Formula III and with $R_3SH$ in the presence of an acidic catalyst and a suitable solvent, wherein:

$R_1$ is alkyl or aryl;

$R_2$ represents 0 to 5 substituents, wherein, in each occurrence, each substituent is independently selected from the group consisting of: alkyl, alkenyl, alkynyl, cycloalkyl, heteroalicyclic, aryl, heteroaryl, hydroxy, alkoxy, aryloxy, thiohydroxy, thioalkoxy, thioaryloxy, halide, amine, amide, carbonyl, thiocarbonyl, carboxy, thiocarboxy, epoxide, sulfonate, sulfonyl, sulfinyl, sulfonamide, nitro, nitrile, isonitrile, thiirane, aziridine, nitroso, hydrazine, sulfate, azide, phosphonyl, phosphinyl, urea, thiourea, carbamyl and thiocarbamyl, fused ring system containing up to three 6-member carbocyclic, each being substituted or non-substituted;

$R_3$ is selected from alkyl, aryl (e.g., phenyl), alkoxy, aryloxy, carbonyl, carboxy, substituted or non-substituted; and $R_4$, $R_5$, and $R_6$ are each independently selected from the group consisting of: hydrogen, alkyl, alkenyl, alkynyl, cycloalkyl, heteroalicyclic, aryl, heteroaryl, hydroxy, alkoxy, aryloxy, thiohydroxy, thioalkoxy, thioaryloxy, halide, amine, amide, carbonyl, thiocarbonyl, carboxy, thiocarboxy, epoxide, sulfonate, sulfonyl, sulfinyl, sulfonamide, nitro, nitrile, isonitrile, thiirane, aziridine, nitroso, hydrazine, sulfate, azide, phosphonyl, phosphinyl, urea, thiourea, carbamyl and thiocarbamyl, thereby forming said compound represented by Formula I.

In some embodiments, $R_3$ is ethyl.

In some embodiments, the acidic catalyst is one or more Lewis acids selected from the group consisting of: $CuCl_2$, $Sc(OTf)_3$, $Fe(OTf)_3$, $In(OTf)_3$, $BF_3 \cdot OEt_2$, and $Cu(OTf)_2$.

In some embodiments, the acidic catalyst is or comprises one or more Brønsted acids selected from Triflic acid (TfOH), para-toluenesulfonic acid, and trifluoroacetic acid.

In some embodiments, the suitable solvent is a polar solvent selected from the group consisting of: acetonitrile, nitromethane, and 2,2,2-trifluoroethanol (TFE), hexafluoroisopropanol (HFIP) or a mixture thereof.

In some embodiments, the process is characterized by at least 30% yield of the compound.

According to an aspect of some embodiments of the present invention, there is provided a product represented by Formula I:

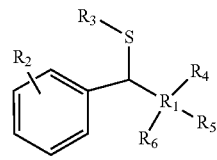

obtained by the process as disclosed herein, wherein $R_1$-$R_6$ are defined hereinabove.

In some embodiments, the product represented by Formula I has the Formula I1:

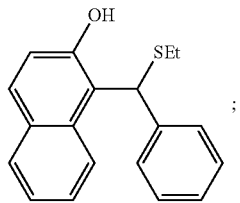

or Formula I2:

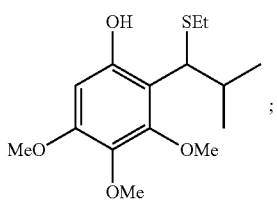

or Formula I3:

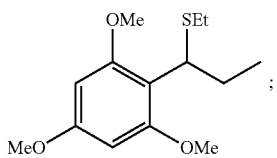

or Formula I4:

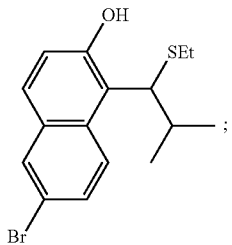

or Formula I5:

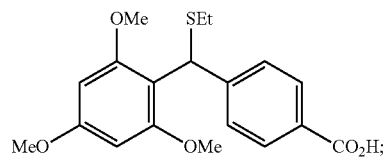

or Formula I6:

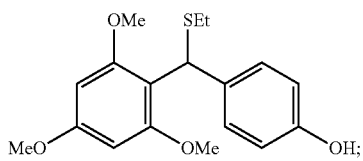

or Formula I7:

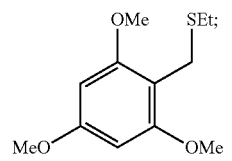

or Formula I8:

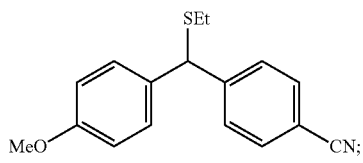

or Formula I9:

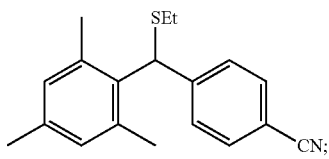

or Formula I10:
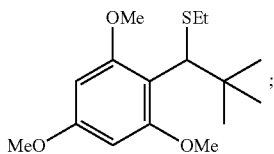
or Formula I11:
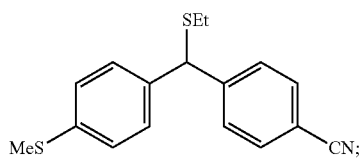
or Formula I12:
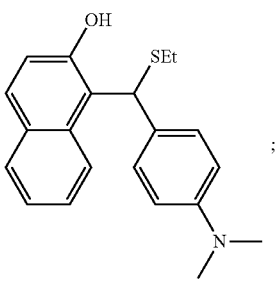
or Formula I13:
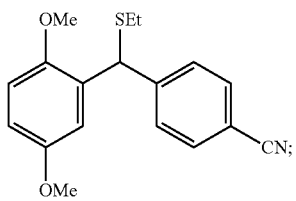
or Formula I14:
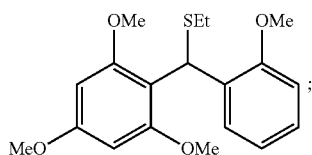
or Formula I15:
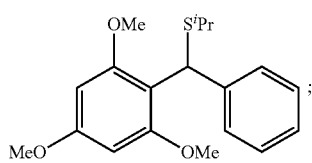
or Formula I16:
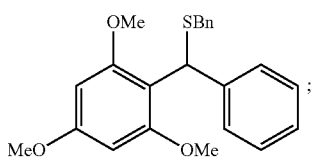
or Formula I17:
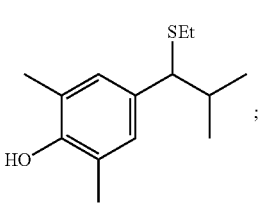
or Formula I18:
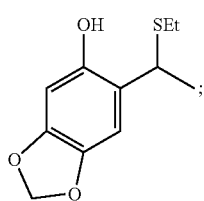
or Formula I19:
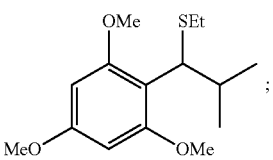
or Formula I20:
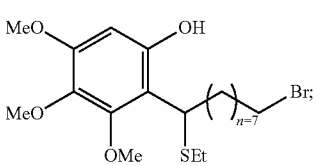
or Formula I21:
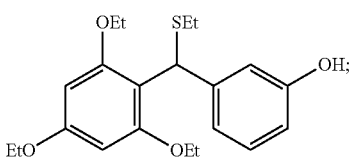

or Formula I22:
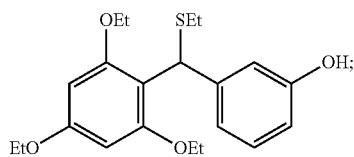
or Formula I23:
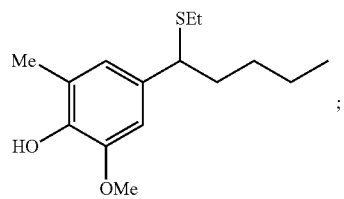
or Formula I24:
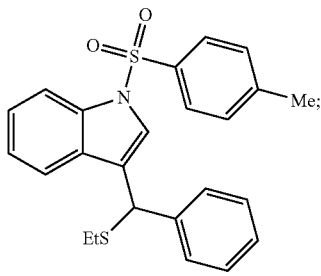
or Formula I25:
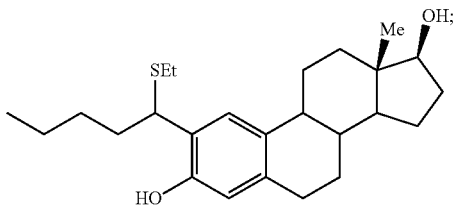
or Formula I26:
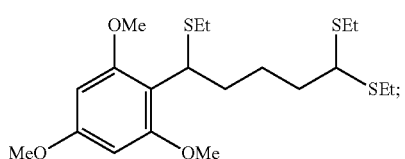
or Formula I27:
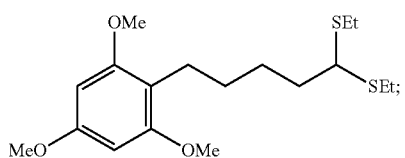
or Formula I28:
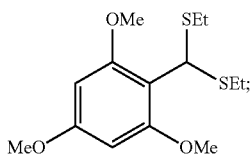
or Formula I29:
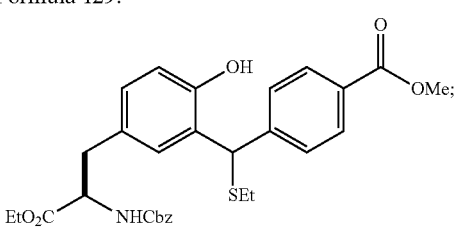
or Formula I30:
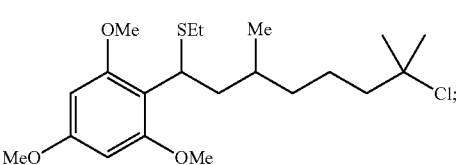
or Formula I31:
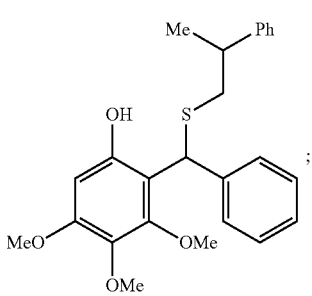 [SMILES: COc1cc(O)c(C(SCC(C)c2ccccc2)c2ccccc2)c(OC)c1OC]
or Formula I32:
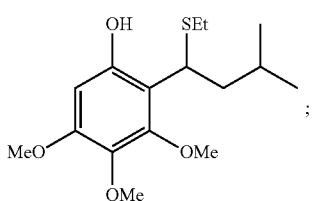
or Formula I33:
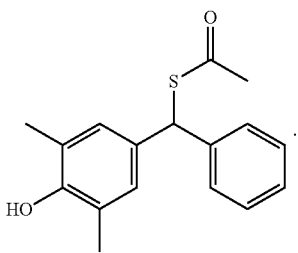 [SMILES: CC(=O)SC(c1ccccc1)c1cc(C)c(O)c(C)c1]

In some embodiments, the process further comprises a subsequent step of reacting the compound represented by Formula I with a reducing agent, thereby forming the compound represented by Formula IV:

Formula IV

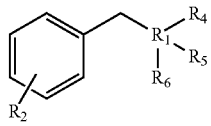

wherein R1-R6 are defined hereinabove.

In some embodiments, the reducing agent is a silane. In some embodiments, the silane is Et$_3$SiH.

In some embodiments, there is provided a product represented by Formula IV obtained following a subsequent step of reacting the compound represented by Formula I with a reducing agent. In some embodiments, the product represented by Formula IV has the Formula IV1:

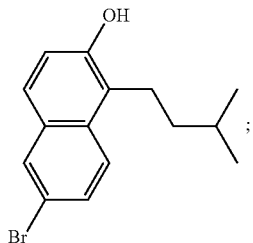 [SMILES: CC(C)CCc1c(O)ccc2cc(Br)ccc12]

or Formula IV2:

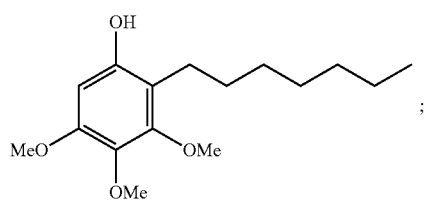 [SMILES: CCCCCCCc1c(O)cc(OC)c(OC)c1OC]

or Formula IV3:

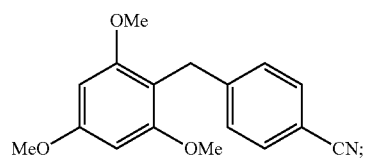 [SMILES: COc1cc(OC)c(Cc2ccc(C#N)cc2)c(OC)c1]

or Formula IV4:

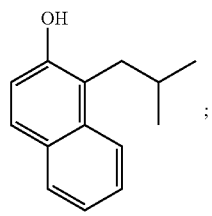

or Formula IV5:

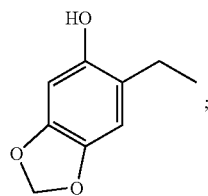

or Formula IV6:

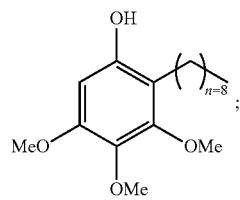

or Formula IV7:

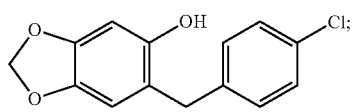 [SMILES: Oc1cc2c(cc1Cc1ccc(Cl)cc1)OCO2]

or Formula IV8:

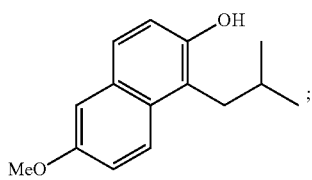 [SMILES: COc1ccc2c(CC(C)C)c(O)ccc2c1]

or Formula IV9:

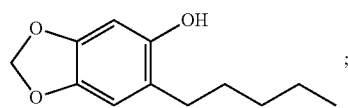

or Formula IV10:

or Formula IV11:

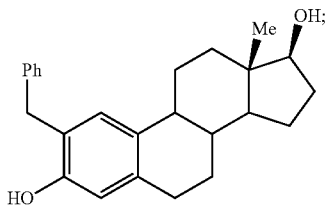 [SMILES: C[C@]12CCC3c4cc(Cc5ccccc5)c(O)cc4CCC3C1CC[C@@H]2O]

or Formula IV12:

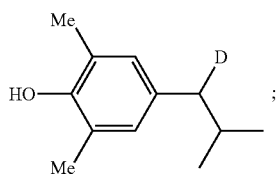

or Formula IV13:

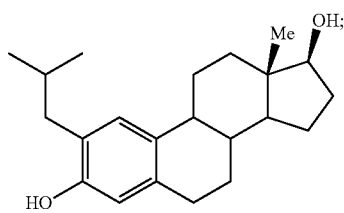 [SMILES: CC(C)Cc1cc2c(cc1O)CCC1C2CC[C@@]2(C)C1CC[C@@H]2O]

or Formula IV14:

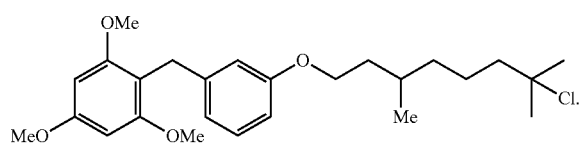 [SMILES: COc1cc(OC)c(Cc2cccc(OCCC(C)CCCC(C)(C)Cl)c2)c(OC)c1]

In some embodiments, there is provided a pharmaceutical composition comprising the product obtained by the disclosed process and represented by Formula IV and a pharmaceutically acceptable excipient.

In some embodiments, there is provided a composition comprising:

(i) one or more Lewis acids selected from the group consisting of: $CuCl_2$, $Sc(OTf)_3$, $Fe(OTf)_3$, $In(OTf)_3$, $BF_3 \cdot OEt_2$, TfOH and $Cu(OTf)_2$;

(ii) a polar solvent selected from the group consisting of: acetonitrile, nitromethane, and 2,2,2-trifluoroethanol (TFE), or a mixture thereof; and (iii) RSH, wherein R is selected from the group consisting of: alkyl, benzyl, alkoxy, aryloxy, carbonyl, carboxy, substituted or non-substituted.

In some embodiments, the Lewis acid is in a molar concentration of at least 1%. In some embodiments, the polar solvent is TFE.

In some embodiments, there is provided a use of a product of formula I and/or a product of formula IV obtained by a process disclosed herein for the preparation of a pharmaceutical composition.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DETAILED DESCRIPTION

Figure 1A:
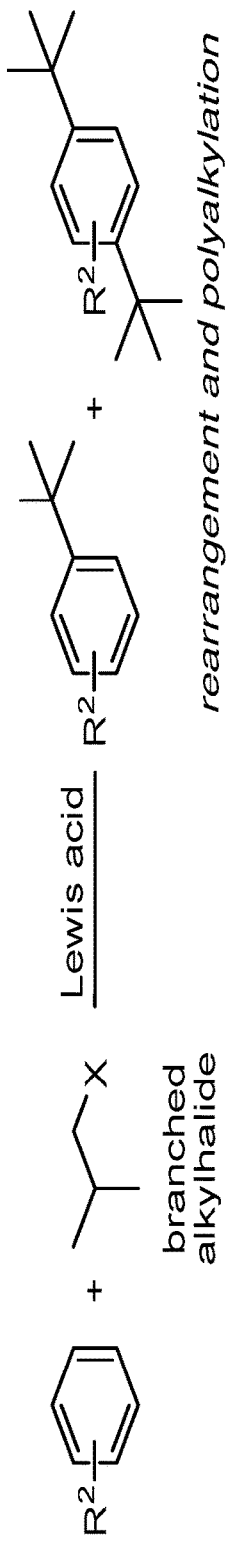
FIGS. 1A-B present Scheme 1A showing a classic Friedel-Craft alkylation (FIG. 1A), and Scheme 1B showing the process of the present invention, in some embodiments thereof (FIG. 1B).

The present invention, in some embodiments thereof, relates to a synthesis route of electrophilic aromatic substitution and, more particularly, but not exclusively, to introducing alkyl groups on one or more aromatic compounds.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

As discussed hereinabove, currently known methodologies of introducing primary alkyl groups on aromatic compounds is a difficult task to achieve. A major limitation lies in the fact that it is unsuitable for primary alkyl halides. The latter react less readily, therefore require harsh conditions and result in a mixture of rearrangement products.

Moreover, the tendency of aliphatic aldehydes to dimerize under acidic conditions prevents the ability to apply them in aromatic electrophilic reactions.

The present invention is based in part on the surprising finding that a highly selective method may be employed for introducing alkyl groups, and particularly, primary alkyl groups on aromatic compounds. The synthesis route is, in some embodiments, is one-pot "Pummerer/Friedel-Crafts" alkylation. In some embodiments, this one-pot alkylation is based on electrophilic aromatic substitution(s) of thionium ion species that is generated in-situ from aldehyde(s) and thiol(s), affording aryl sulfide. Aryl sulfide can be then reduced with triethylsilane. In some embodiments, this one-pot alkylation is suitable for aromatic compounds and both linear and branched aliphatic aldehydes. In some embodiments, the alkylation is performed under air and in the presence of water and various functional groups.

In some embodiments, the disclosed reaction is compatible with a variety of functionalities and reagents (including, without limitation, alkyl halides, which are the substrates of the classic Friedel-Crafts reaction). In some embodiments, the disclosed reaction is water tolerant. In some embodiments, the disclosed reaction avoids the use of corrosive reagents and toxic halides, and can be applied to key biologically active compounds.

The Process:

According to some aspects, the present invention provides a process for synthesis of a compound represented by Formula I (designated as: "compound I"):

Formula I

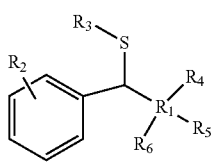

In some embodiments, the process comprises:
reacting a compound represented by Formula II (designated as: "compound II" and also referred to as "the aldehyde"):

Formula II

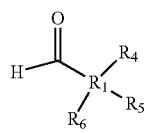

with a compound represented by Formula III (designated as: "compound III"):

Formula III

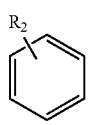

and with $R_3SH$, wherein:

$R_1$ is alkyl or aryl;

$R_2$ represents 0 to 5 substituents, wherein, in each occurrence, each substituent is independently selected from the group consisting of: alkyl, alkenyl, alkynyl, cycloalkyl, heteroalicyclic, aryl, heteroaryl, hydroxy, alkoxy, aryloxy, thiohydroxy, thioalkoxy, thioaryloxy, halide, amine, amide, carbonyl, thiocarbonyl, carboxy, thiocarboxy, epoxide, sulfonate, sulfonyl, sulfinyl, sulfonamide, nitro, nitrile, isonitrile, thiirane, aziridine, nitroso, hydrazine, sulfate, azide, phosphonyl, phosphinyl, urea, thiourea, carbamyl and thiocarbamyl, fused ring system containing up to three 6-member carbocyclic, each being substituted or non-substituted;

$R_3$ is selected from alkyl, aryl (e.g., phenyl), alkoxy, aryloxy, carbonyl, carboxy, substituted or non-substituted;

$R_4$, $R_5$, and $R_6$ are each, independently, selected from the group consisting of: hydrogen, alkyl, alkenyl, alkynyl, cycloalkyl, heteroalicyclic, aryl, heteroaryl, hydroxy, alkoxy, aryloxy, thiohydroxy, thioalkoxy, thioaryloxy, halide, amine, amide, carbonyl, thiocarbonyl, carboxy, thiocarboxy, epoxide, sulfonate, sulfonyl, sulfinyl, sulfonamide, nitro, nitrile, isonitrile, thiirane, aziridine, nitroso, hydrazine, sulfate, azide, phosphonyl, phosphinyl, urea, thiourea, carbamyl and thiocarbamyl, to thereby form the compound represented by Formula I.

In some embodiments, the process is performed in the presence of an acidic catalyst and/or in a suitable solvent.

As used herein and in the art, the term "catalyst" refers to a substance which initiates or accelerates a chemical reaction.

In some embodiments, the acidic catalyst is one or more Lewis acids. As used herein and in the art, "Lewis acid" refers to a powerful electron pair acceptor.

Exemplary Lewis acids include, but are not limited to, $CuCl_2$, $Sc(OTf)_3$, $Fe(OTf)_3$, $In(OTf)_3$, $BF_3 \cdot OEt_2$, and $Cu(OTf)_2$.

In some embodiments, the acidic catalyst is or comprises one or more Brønsted acids.

As used herein and in the art, "Brønsted acid" refers to a compound that is capable of donating a proton ($H^+$) to another compound. Exemplary Brønsted acids include, but are not limited to, Triflic acid (TfOH), para-toluenesulfonic acid, and trifluoroacetic acid.

In some embodiment, the reaction process is performed in a mild acidic condition. By "mild acidic condition" it is meant that the molar concentration of the acid in the solvent is e.g., about 0.25%, about 0.5%, about 1.75%, about 2%, about 2.25%, about 2.5%, about 2.75%, about 3%, about 3.25%, about 3.5%, about 3.75%, about 4%, about 4.25%, about 4.5%, about 4.75%, about 5%, about 5.25%, about 5.5%, about 5.75%, about 6%, about 6.25%, about 6.5%, about 6.75%, about 7%, about 7.25%, about 7.5%, about 7.75%, about 8%, about 8.25%, about 8.5%, about 8.75%, about 9%, about 9.25%, about 9.5%, about 9.75%, or about 10%, including any value and range therebetween. Each possibility represents a separate embodiment of the present invention.

In some embodiments, the process (i.e. the synthesis procedure) is performed at a temperature that ranges from 10° C. to 90° C. In some embodiments, the reaction process is performed at a temperature that ranges from 20° C. to 70° C., or e.g., from 25° C. to 45° C., or from 30° C. to 50° C.

In some embodiments, the reaction time is at least 1 minute. In some embodiments, the reaction time is e.g., at least 5 minutes, at least 10 minutes, at least 15 minutes, at least 20 minutes, at least 25 minutes, at least 30 minutes, at least 35 minutes, at least 40 minutes, at least 45 minutes, at least 50 minutes, at least 55 minutes, at least 60 minutes, at least 65 minutes, at least 70 minutes, at least 75 minutes, or at least 80 minutes. Each possibility represents a separate embodiment of the present invention.

In some embodiments, the reaction time is at least 1 hour. In some embodiments, the reaction time is e.g., at least 2 hours, at least 3 hours, at least 4 hours, at least 5 hours, at least 6 hours, at least 7 hours, at least 8 hours, at least 9 hours, at least 10 hours, at least 11 hours, at least 12 hours, at least 13 hours, at least 14 hours, at least 15 hours, at least 16 hours, at least 17 hours, at least 18 hours, at least 19 hours, at least 20 hours, at least 21 hours, at least 22 hours, at least 23 hours, or at least 24 hours. Each possibility represents a separate embodiment of the present invention.

It is noteworthy that contrary to the classic Friedel-Crafts alkylation, which requires anhydrous conditions, the electrophilic aromatic substitution underlying the synthesis route disclosed hereinthroughout can be carried out in water, as exemplified in the Example section.

In some embodiments, the synthesis route disclosed hereinthroughout enables mono-substitution of the alkyl scaffold to an aromatic compound. In some embodiments, the alkyl scaffold maintains its original structure.

An exemplary embodiment of the synthesis route of the invention is described in the Examples section below.

It is also of note that the aldehyde (e.g., compound II) in the synthesis route disclosed herein may be either linear or branched.

In some embodiments the synthesis route disclosed hereinthroughout is characterized by a yield of e.g., about 10%, about 20%, about 30%, about 40%, about 50%, about 60%, about 70%, about 80%, about 90%, about 100%, including any value and range therebetween, based on the initial molar of the arene.

In some embodiment, the suitable solvent is a polar solvent. By "polar solvent", it is meant to include any solvent that exhibits polar forces on solutes, due to high dipole moment, wide separation of charges, or tight association.

Exemplary polar solvents include, but are not limited to, acetonitrile, nitromethane, and 2,2,2-trifluoroethanol (TFE), nitrobenzene, hexa-fluoro-isopropanol (HFIP) or a mixture thereof.

Without being bound by any particular theory, it is assumed that the disclosed synthesis route is based on electrophilic aromatic substitutions of thionium ion species, transformed from aldehydes and thiols under the acid-catalyzed conditions, as described hereinbelow in the Example section. This transformation affords e.g., 1-(ethyl-thio)benzyl and alkylarenes in high chemo- and regioselectivity, which can be reduced e.g., in situ, to the corresponding saturated alkyl arenes, as summarizes in Scheme 1B in the Example section.

In some embodiments, the $R_2$ substituent is absent. In some embodiments, $R_2$ represents one substituent of alkyl. In some embodiments, $R_2$ represents two substituents of alkyl. In some embodiments, $R_2$ represents three substituents of alkyl.

In some embodiments, $R_2$ represents one substituent of ethoxy. In some embodiments, $R_2$ represents two substituents of ethoxy. In some embodiments, $R_2$ represents three substituents of ethoxy.

In some embodiments, $R_2$ is one substituent of 4-methoxy ("4-OMe"; herein the "number-" represents the position in respects to the thiol group in the compound of the product represented by Formula I)). In some embodiments, $R_2$ represents one substituent of 4-SMe. In some embodiments, $R_2$ represents two substituents of 2,5-di-OMe. In some embodiments, $R_2$ represents three substituents of 2,4,6-tri-Me. In some embodiments, $R_2$ represents three substituents of 2,4,6-tri-OMe. In some embodiments, $R_2$ represents 2-naphthalene fused at position 2.

In some embodiments, $R_3$ is ethyl. In some embodiments, $R_3$ is isopropyl (iPr). In some embodiments, $R_3$ is benzyl (Bn). In some embodiments, $R_3$ is acyl (carbonyl).

In some embodiments, $R_1$ is alkyl, substituted or non-substituted. In some embodiments, $R_1$ is methyl. In some embodiments, $R_1$ is aryl. In some embodiments, $R_1$ is bulky, for example, branched alkyl, branched alkenyl or branched alkynyl and/or a cyclic moiety. In some embodiments, the bulky moiety is a cyclic moiety selected from the group consisting of cycloalkyl, heteroalicyclic, aryl and heteroaryl, each being substituted or non-substituted.

In some embodiments, one or more (e.g., two) of $R_4$, $R_5$ and $R_6$ groups are each independently selected from the group consisting of: hydrogen, alkyl, alkenyl, alkynyl, cycloalkyl, heteroalicyclic, aryl, heteroaryl, hydroxy, alkoxy, aryloxy, thiohydroxy, thioalkoxy, thioaryloxy, halide, amine, amide, carbonyl, thiocarbonyl, carboxy, thiocarboxy, epoxide, sulfonate, sulfonyl, sulfinyl, sulfonamide, nitro, nitrile, isonitrile, thiirane, aziridine, nitroso, hydrazine, sulfate, azide, phosphonyl, phosphinyl, urea, thiourea, carbamyl and thiocarbamyl, a fused ring system containing up to three 6-member carbocyclic, each being substituted or non-substituted.

In some embodiments, one or more (e.g., two) of $R_4$, $R_5$ and $R_6$ groups are hydrogen atoms. In some embodiments, two of $R_4$, $R_5$ and $R_6$ groups are hydrogen atoms. In some embodiments, two of $R_4$, $R_5$ and $R_6$ groups are hydrogen atoms and one of $R_4$, $R_5$ and $R_6$ groups are selected from: hydroxyl, —CO$_2$H, —CN, —OMe, halide, —CN, —NMe$_2$. In some embodiments, the halide is bromide.

In some embodiments, the synthesis is performed such that the molar ratio of $R_3$SH and compound II at the beginning of the reaction is e.g., 1:1, 1:2, 1:3, 1:4, 1:5, 1:6, 1:7, 1:8, 1:9, 1:10, including any value therebetween. Each possibility represents a separate embodiment of the present invention.

In exemplary embodiments, the molar ratio of $R_3$SH and compound II at the beginning of the reaction is 1:2, respectively. In additional exemplary embodiments, the molar ratio of $R_3$SH and compound II at the beginning of the reaction is 1:3, respectively.

In some embodiments, the synthesis is performed such that the molar ratio of compound III and compound II is e.g., 1:1, 1:2, 1:3, 1:4, 1:5, 1:6, 1:7, 1:8, 1:9, or 1:10, including any value therebetween. In exemplary embodiments, the molar ratio is about 1:2.

In some embodiments, the present invention provides a process for the preparation of a compound of formula I1:

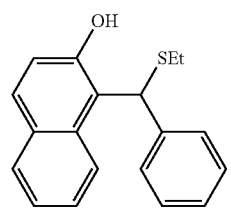

In some embodiments, the present invention provides a process for the preparation of a compound of formula I2:

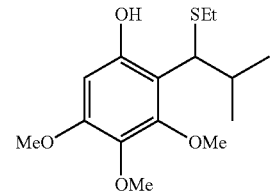

In some embodiments, the present invention provides a process for the preparation of a compound of formula I3:

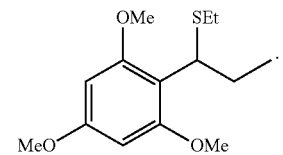

In some embodiments, the present invention provides a process for the preparation of a compound of formula I4:

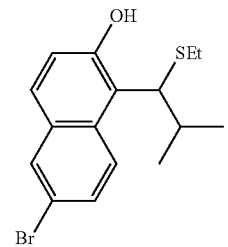

In some embodiments, the present invention provides a process for the preparation of a compound of formula I5:

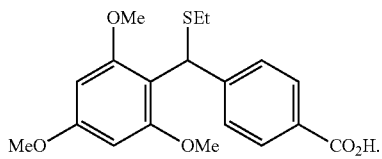

In some embodiments, the present invention provides a process for the preparation of a compound of formula I6:

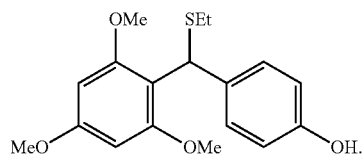

In some embodiments, the present invention provides a process for the preparation of a compound of formula I7:

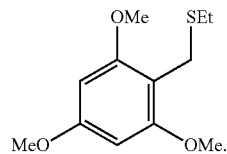

In some embodiments, the present invention provides a process for the preparation of a compound of formula I8:

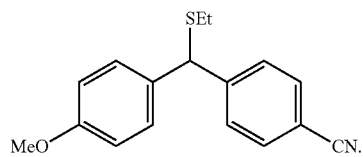

In some embodiments, the present invention provides a process for the preparation of a compound of formula I9:

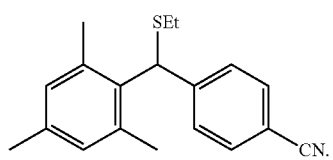

In some embodiments, the present invention provides a process for the preparation of a compound of formula I10:

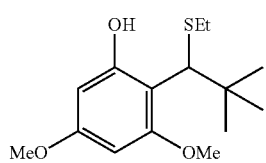

In some embodiments, the present invention provides a process for the preparation of a compound of formula I11:

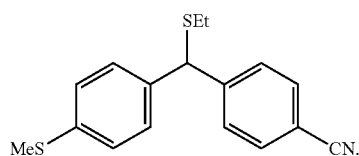

In some embodiments, the present invention provides a process for the preparation of a compound of formula I12:

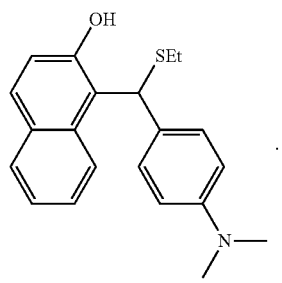

In some embodiments, the present invention provides a process for the preparation of a compound of formula I13:

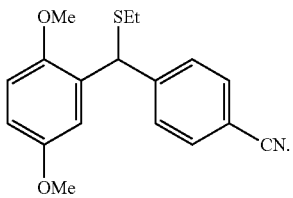

In some embodiments, the present invention provides a process for the preparation of a compound of formula I14:

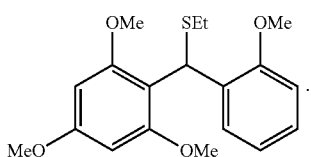

In some embodiments, the present invention provides a process for the preparation of a compound of formula I15:

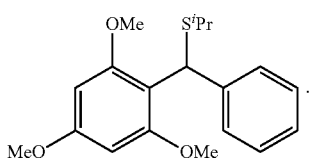

In some embodiments, the present invention provides a process for the preparation of a compound of formula I16:

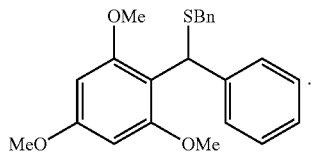

In some embodiments, the present invention provides a process for the preparation of a compound of formula I17:

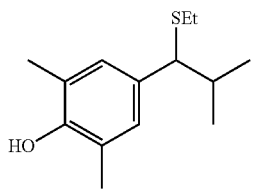

In some embodiments, the present invention provides a process for the preparation of a compound of formula I18:

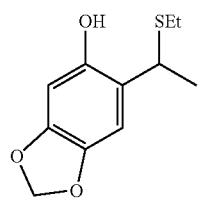

In some embodiments, the present invention provides a process for the preparation of a compound of formula I19:

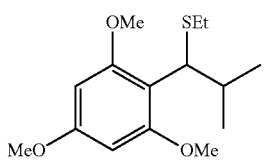

In some embodiments, the present invention provides a process for the preparation of a compound of formula I20:

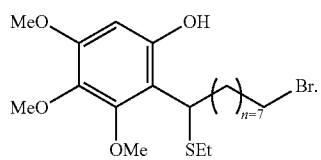

In some embodiments, the present invention provides a process for the preparation of a compound of formula I21:

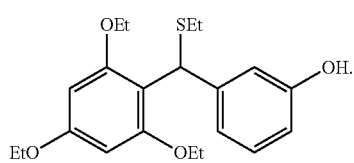

In some embodiments, the present invention provides a process for the preparation of a compound of formula I22:

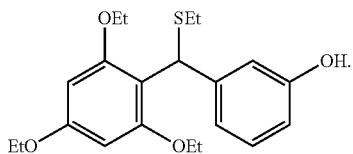

In some embodiments, the present invention provides a process for the preparation of a compound of formula I23:

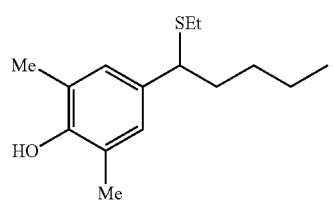

In some embodiments, the present invention provides a process for the preparation of a compound of formula I24:

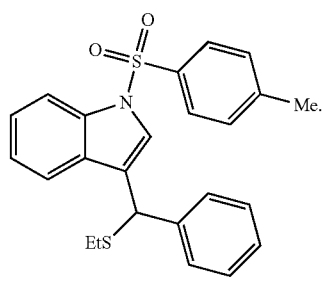

In some embodiments, the present invention provides a process for the preparation of a compound of formula I25:

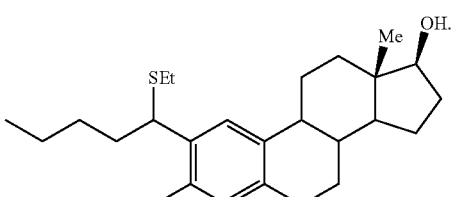

In some embodiments, the present invention provides a process for the preparation of a compound of formula I26:

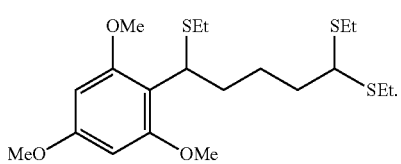

In some embodiments, the present invention provides a process for the preparation of a compound of formula I27:

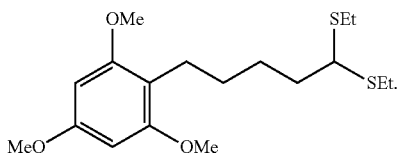

In some embodiments, the present invention provides a process for the preparation of a compound of formula I28:

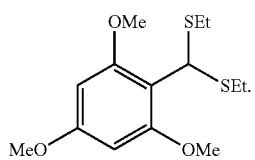

In some embodiments, the present invention provides a process for the preparation of a compound of formula I29:

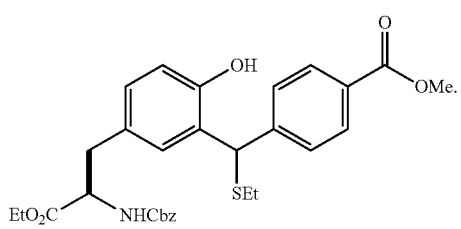

In some embodiments, the present invention provides a process for the preparation of a compound of formula I30:

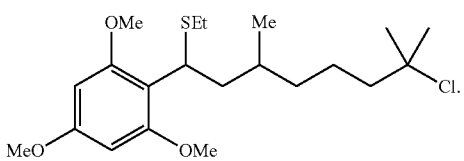

In some embodiments, the present invention provides a process for the preparation of a compound of formula I31:

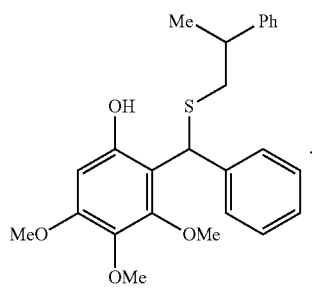 [SMILES: COc1cc(O)c(C(SCC(C)c2ccccc2)c2ccccc2)c(OC)c1OC]

In some embodiments, the present invention provides a process for the preparation of a compound of formula I32:

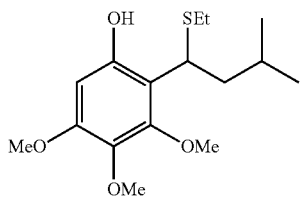

In some embodiments, the present invention provides a process for the preparation of a compound of formula I33:

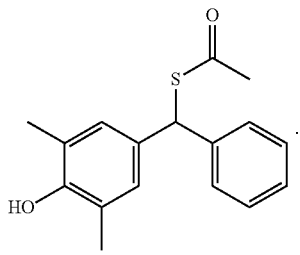 [SMILES: CC(=O)SC(c1ccccc1)c1cc(C)c(O)c(C)c1]

In some embodiments, the synthesis further comprises a subsequent step of oxidation or a step of reduction of the sulfide of compound represented by Formula I.

In some embodiments, the subsequent step is reduction of the sulfide of compound represented by Formula I.

In some embodiments, the subsequent step is performed in in-situ fashion.

In some embodiments, the subsequent step of reduction of the sulfide comprises reacting the compound represented by Formula I, with one or more reducing agents (also referred to as: "reduction step"), thereby forming the compound represented by Formula IV.

In some embodiments, the subsequent step of the reduction is performed in a one-pot follow-up procedure.

The term "one-pot", as used herein, refers to a process for preparing a desired product, comprising simultaneously or successively adding all reactants into a reactor to have them react together, in which no separation and/or purification of the intermediate formed is needed before the product is produced.

In some embodiments, the reducing agent is a silane. In some embodiments, the silane has the formula: $(alkyl)_3SiH$, wherein each alkyl is independently as defined hereinthroughout. In some embodiments, the silane is $Et_3SiH$.

In some embodiments, the silane has the formula: $Ar_3SiH$, wherein Ar is aryl (also termed: "arene") as defined hereinthroughout.

In some embodiments, the reduction step is preformed such that compound I, and $Et_3SiH$ are in at molar ratio of e.g., at least 1:1, at least 1:2, at least 1:3, including any value therebetween.

In some embodiments, the subsequent step is performed in in-situ fashion. In some embodiments, the subsequent step is performed step-wise.

In some embodiments, the subsequent step is preformed in a solution comprising a catalyst. Exemplary catalysts are described hereinabove.

In some embodiments, the subsequent step is preformed in a solution comprising any polar solvent as defined hereinabove.

In exemplary embodiments, the compound represented by Formula IV, (obtained following the subsequent step) is IV1:

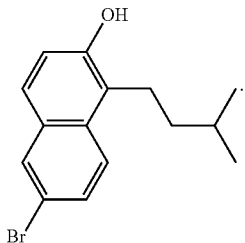

In exemplary embodiments, the compound represented by Formula IV is IV2:

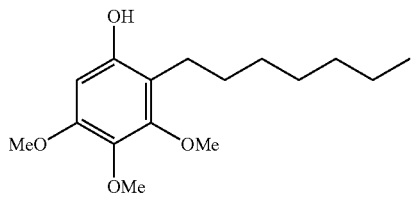

In exemplary embodiments, the compound as represented by Formula IV is IV3:

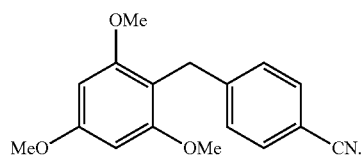 [SMILES: COc1cc(OC)c(Cc2ccc(C#N)cc2)c(OC)c1]

In exemplary embodiments, the compound as represented by Formula IV is IV4:

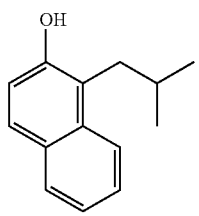

In exemplary embodiments, the compound as represented by Formula IV is IV5:

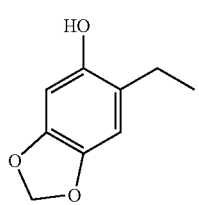

In exemplary embodiments, the compound as represented by Formula IV is IV6:

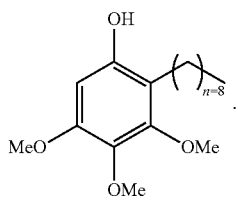

In exemplary embodiments, the compound as represented by Formula IV is IV7:

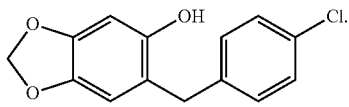 [SMILES: Oc1cc2c(cc1Cc1ccc(Cl)cc1)OCO2]

In exemplary embodiments, the compound as represented by Formula IV is IV8:

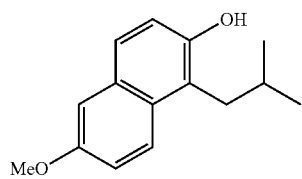

In exemplary embodiments, the compound as represented by Formula IV is IV9:

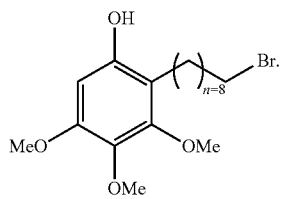

In exemplary embodiments, the compound as represented by Formula IV is IV10:

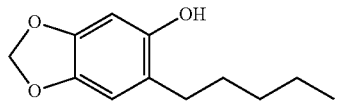

In exemplary embodiments, the compound as represented by Formula IV is IV11:

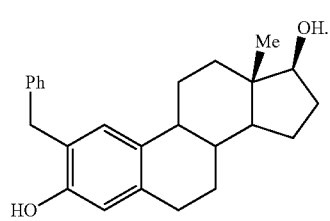 [SMILES: C[C@]12CCC3c4cc(Cc5ccccc5)c(O)cc4CCC3C1CC[C@@H]2O]

In exemplary embodiments, the compound as represented by Formula IV is IV12:

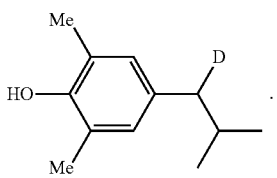

In exemplary embodiments, the compound as represented by Formula IV is IV13:

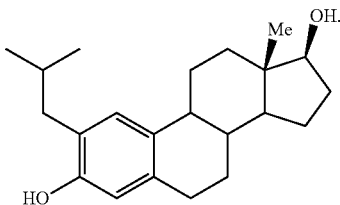 [SMILES: CC(C)Cc1cc2c(cc1O)CCC1C2CC[C@@]2(C)C1CC[C@@H]2O]

In exemplary embodiments, the compound as represented by Formula IV is IV14:

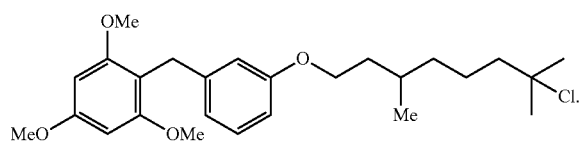 [SMILES: COc1cc(OC)c(Cc2cccc(OCCC(C)CCCC(C)(C)Cl)c2)c(OC)c1]

As used herein, the term "alkyl" describes an aliphatic hydrocarbon including straight chain and branched chain groups. Preferably, the alkyl group has 21 to 100 carbon atoms, and more preferably 21-50 carbon atoms. Whenever a numerical range; e.g., "21-100", is stated herein, it implies that the group, in this case the alkyl group, may contain 21 carbon atom, 22 carbon atoms, 23 carbon atoms, etc., up to and including 100 carbon atoms. In the context of the present invention, a "long alkyl" is an alkyl having at least 20 carbon atoms in its main chain (the longest path of continuous covalently attached atoms). A short alkyl therefore has 20 or less main-chain carbons. The alkyl can be substituted or unsubstituted, as defined herein. The alkyl group may be substituted or unsubstituted. When substituted, the substituent group can be, for example, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, sulfonate, nitrile, nitro, azide, phosphonyl, phosphinyl, oxo, carbonyl, thiocarbonyl, urea, thiourea, carbamyl, N-carbamyl, O-thiocarbamyl, N-thiocarbamyl, C-amido, N-amido, C-carboxy, O-carboxy, sulfonamide, and amino, as these terms are defined herein.

The term "alkyl", as used herein, also encompasses saturated or unsaturated hydrocarbon, hence this term further encompasses alkenyl and alkynyl.

The term "alkenyl" describes an unsaturated alkyl, as defined herein, having at least two carbon atoms and at least one carbon-carbon double bond. The alkenyl may be substituted or unsubstituted by one or more substituents, as described hereinabove.

The term "alkynyl", as defined herein, is an unsaturated alkyl having at least two carbon atoms and at least one carbon-carbon triple bond. The alkynyl may be substituted or unsubstituted by one or more substituents, as described hereinabove.

The term "cycloalkyl" describes an all-carbon monocyclic or fused ring (i.e., ring that shares an adjacent pair of carbon atoms) group where one or more of the rings does not have a completely conjugated pi-electron system. The cycloalkyl group may be substituted or unsubstituted, as indicated herein.

The term "aryl" describes an all-carbon monocyclic or fused-ring polycyclic (i.e., rings which share adjacent pairs of carbon atoms) groups having a completely conjugated pi-electron system. The aryl group may be substituted or unsubstituted, as indicated herein.

The term "alkoxy" describes both an —O-alkyl and an —O-cycloalkyl group, as defined herein.

The term "aryloxy" describes an —O-aryl, as defined herein.

Each of the alkyl, cycloalkyl and aryl groups in the general formulas herein may be substituted by one or more substituents, whereby each substituent group can independently be, for example, halide, alkyl, alkoxy, cycloalkyl, alkoxy, nitro, amine, hydroxyl, thiol, thioalkoxy, thiohydroxy, carboxy, amide, aryl and aryloxy, depending on the substituted group and its position in the molecule. Additional substituents are also contemplated The term "halide", "halogen" or "halo" describes fluorine, chlorine, bromine or iodine.

The term "haloalkyl" describes an alkyl group as defined herein, further substituted by one or more halide(s).

The term "hydroxyl" or "hydroxy" describes a —OH group.

The term "thiohydroxy" or "thiol" describes a —SH group.

The term "thioalkoxy" describes both an —S-alkyl group, and a —S-cycloalkyl group, as defined herein.

The term "thioaryloxy" describes both an —S-aryl and a —S-heteroaryl group, as defined herein.

The term "amine" describes a —NR'R" group, with R' and R" as described herein.

The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine.

The term "heteroalicyclic" or "heterocyclyl" describes a monocyclic or fused ring group having in the ring(s) one or more atoms such as nitrogen, oxygen and sulfur. The rings may also have one or more double bonds. However, the rings do not have a completely conjugated pi-electron system. Representative examples are piperidine, piperazine, tetrahydrofurane, tetrahydropyrane, morpholino and the like.

The term "carboxy" or "carboxylate" describes a —C(=O)—OR' group, where R' is hydrogen, alkyl, cycloalkyl, alkenyl, aryl, heteroaryl (bonded through a ring carbon) or heteroalicyclic (bonded through a ring carbon) as defined herein.

The term "carbonyl" describes a —C(=O)—R' group, where R' is as defined hereinabove.

The above-terms also encompass thio-derivatives thereof (thiocarboxy and thiocarbonyl).

The term "thiocarbonyl" describes a —C(=S)—R' group, where R' is as defined hereinabove.

A "thiocarboxy" group describes a —C(=S)—OR' group, where R' is as defined herein.

A "sulfinyl" group describes an —S(=O)—R' group, where R' is as defined herein.

A "sulfonyl" or "sulfonate" group describes an —S(=O)$_2$—R' group, where Rx is as defined herein.

A "carbamyl" or "carbamate" group describes an —OC(=O)—NR'R" group, where R' is as defined herein and R" is as defined for R'.

A "nitro" group refers to a —NO$_2$ group.

A "cyano" or "nitrile" group refers to a —C≡N group.

As used herein, the term "azide" refers to a —N$_3$ group.

The term "sulfonamide" refers to a —S(=O)$_2$—NR'R" group, with R' and R" as defined herein.

The term "phosphonyl" or "phosphonate" describes an —O—P(=O)(OR')$_2$ group, with R' as defined hereinabove.

The term "phosphinyl" describes a —PR'R" group, with R' and R" as defined hereinabove.

The term "alkaryl" describes an alkyl, as defined herein, which substituted by an aryl, as described herein. An exemplary alkaryl is benzyl.

The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine. The heteroaryl group may be substituted or unsubstituted by one or more substituents, as described hereinabove. Representative examples are thiadiazole, pyridine, pyrrole, oxazole, indole, purine and the like.

As used herein, the terms "halo" and "halide", which are referred to herein interchangeably, describe an atom of a halogen, that is fluorine, chlorine, bromine or iodine, also referred to herein as fluoride, chloride, bromide and iodide.

The term "haloalkyl" describes an alkyl group as defined above, further substituted by one or more halide(s).

Pharmaceutical Composition:

According to an aspect of embodiments of the invention there is provided a pharmaceutical composition comprising one or more compounds produced by the process disclosed herein, and a pharmaceutically acceptable carrier.

Exemplary compounds include drugs and natural products known in the art, having attached with alkyl substituents, including, for example and without limitation, Ibuprofen, Beclorbrate, Captodiamine, and Montelukast:

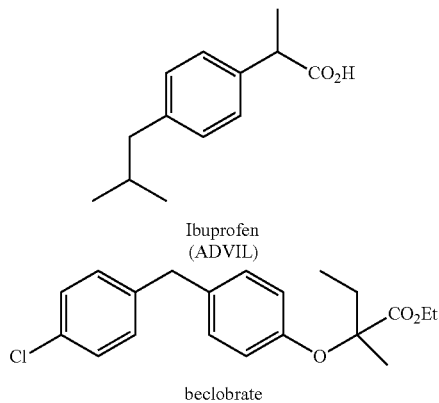

Ibuprofen (ADVIL)

beclobrate

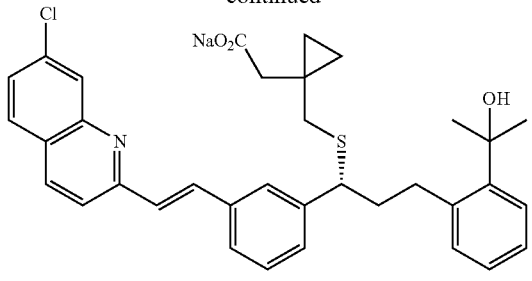

Montelukast

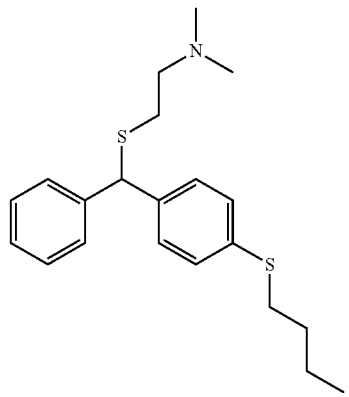

Captodiame

According to some embodiments of the invention, the composition is being packaged in a packaging material and identified in print, in or on the packaging material, for use in the treatment of a medical condition associated with any disease, medical condition, or disorder.

According to an aspect of embodiments of the invention there is provided a use of any one of the compound described herein as a medicament.

According to an aspect of embodiments of the invention there is provided a use of any one of the compound described herein in the manufacture of a medicament for treating a medical condition associated with a disease, medical condition, or disorder.

The compounds described hereinabove may be administered or otherwise utilized in this and other aspects of the present invention, either as is, or as a pharmaceutically acceptable salt, enantiomer, diastereomer, solvate, hydrate or a prodrug thereof.

The phrase "pharmaceutically acceptable salt" refers to a charged species of the parent compound and its counter ion, which is typically used to modify the solubility characteristics of the parent compound and/or to reduce any significant irritation to an organism by the parent compound, while not abrogating the biological activity and properties of the administered compound. The neutral forms of the compounds may be regenerated by contacting the salt with a base or acid and isolating the parent compound in a conventional manner. The parent form of the compound differs from the various salt forms in certain physical properties, such as solubility in polar solvents, but otherwise the salts are equivalent to the parent form of the compound for the purposes of the present invention. The phrase "pharmaceutically acceptable salts" is meant to encompass salts of the active compounds that are prepared with relatively nontoxic acids or bases, depending on the particular substituents found on the compounds described herein.

Non-limiting examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", Journal of Pharmaceutical Science, 1977, 66, 1-19). Certain specific compounds of the present invention contain both basic and acidic functionalities that allow one or more compounds described herein to be converted into either base or acid addition salts.

The neutral forms of the compounds as described herein are preferably regenerated by contacting the salt with a base or acid and isolating the parent compounds in a conventional manner.

The term "prodrug" refers to an agent, which is converted into the active compound (the active parent drug) in vivo. Prodrugs are typically useful for facilitating the administration of the parent drug. The prodrug may also have improved solubility as compared with the parent drug in pharmaceutical compositions. Prodrugs are also often used to achieve a sustained release of the active compound in vivo.

The compounds described herein may possess asymmetric carbon atoms (optical centers) or double bonds; the racemates, diastereomers, geometric isomers and individual isomers are encompassed within the scope of the present invention.

As used herein, the term "enantiomer" describes a stereoisomer of a compound that is superposable with respect to its counterpart only by a complete inversion/reflection (mirror image) of each other. Enantiomers are said to have "handedness" since they refer to each other like the right and left hand. Enantiomers have identical chemical and physical properties except when present in an environment which by itself has handedness, such as all living systems.

The compounds described herein can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

The term "solvate" refers to a complex of variable stoichiometry (e.g., di-, tri-, tetra-, penta-, hexa-, and so on), which is formed by a solute (the conjugate described herein) and a solvent, whereby the solvent does not interfere with the biological activity of the solute. Non-limiting exemplary suitable solvents include, for example, ethanol, acetic acid and the like.

The term "hydrate" refers to a solvate, as defined hereinabove, where the solvent is water.

According to another aspect of embodiments of the invention there is provided a pharmaceutical composition comprising, as an active ingredient, any of the compounds described herein produced by the disclosed process and a pharmaceutically acceptable carrier.

Accordingly, in any of the methods and uses described herein, any of the compounds described herein can be provided to an individual either per se, or as part of a pharmaceutical composition where it is mixed with a pharmaceutically acceptable carrier.

As used herein a "pharmaceutical composition" refers to a preparation of one or more of the compounds described herein (as active ingredient), or physiologically acceptable salts or prodrugs thereof, with other chemical components including, but not limited to, physiologically suitable carriers, excipients, lubricants, buffering agents, antimicrobial agents, bulking agents (e.g. mannitol), antioxidants (e.g., ascorbic acid or sodium bisulfite), anti-inflammatory agents, anti-viral agents, chemotherapeutic agents, anti-histamines and the like. The purpose of a pharmaceutical composition is to facilitate administration of a compound to a subject. The term "active ingredient" refers to a compound, which is accountable for a biological effect.

The terms "physiologically acceptable carrier" and "pharmaceutically acceptable carrier", which may be interchangeably used, refer to a carrier or a diluent that does not cause significant irritation to an organism and does not abrogate the biological activity and properties of the administered compound.

Herein the term "excipient" refers to an inert substance added to a pharmaceutical composition to further facilitate administration of a drug. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences" Mack Publishing Co., Easton, Pa., latest edition, which is incorporated herein by reference.

Pharmaceutical compositions for use in accordance with the present invention thus may be formulated in conventional manner using one or more pharmaceutically acceptable carriers comprising excipients and auxiliaries, which facilitate processing of the compounds into preparations which can be used pharmaceutically. Proper formulation is dependent upon the route of administration chosen. The dosage may vary depending upon the dosage form employed and the route of administration utilized. The exact formulation, route of administration and dosage can be chosen by the individual physician in view of the patient's condition (see e.g., Fingl et al., 1975, in "The Pharmacological Basis of Therapeutics", Ch. 1 p. 1).

The pharmaceutical composition may be formulated for administration in either one or more of routes depending on whether local or systemic treatment or administration is of choice, and on the area to be treated. Administration may be done orally, by inhalation, or parenterally, for example by intravenous drip or intraperitoneal, subcutaneous, intramuscular or intravenous injection, or topically (including ophthalmically, vaginally, rectally, intranasally).

Formulations for topical administration may include but are not limited to lotions, ointments, gels, creams, suppositories, drops, liquids, sprays and powders. Conventional pharmaceutical carriers, aqueous, powder or oily bases, thickeners and the like may be necessary or desirable.

Compositions for oral administration include powders or granules, suspensions or solutions in water or non-aqueous media, sachets, pills, caplets, capsules or tablets. Thickeners, diluents, flavorings, dispersing aids, emulsifiers or binders may be desirable.

Formulations for parenteral administration may include, but are not limited to, sterile solutions that may also contain buffers, diluents and other suitable additives. Slow release compositions are envisaged for treatment.

The amount of a composition to be administered will, of course, be dependent on the subject being treated, the severity of the affliction, the manner of administration, the judgment of the prescribing physician, etc.

The pharmaceutical composition may further comprise additional pharmaceutically active or inactive agents such as, but not limited to, an antibacterial agent, an antioxidant, a buffering agent, a bulking agent, a surfactant, an anti-inflammatory agent, an anti-viral agent, a chemotherapeutic agent and an anti-histamine.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

Agrochemical Composition:

According to an aspect of embodiments of the invention there is provided an agrochemical composition comprising one or more compounds as described herein.

Herein, with respect to the field and art of the present invention, an 'agrochemical' is to be understood as generally being any chemical, biological, or/and physical, entity, structure, substance, material, compound, composition, formulation, or organism, singly or in combination, which is applied or dispensed to, or/and upon, the outer (air or atmosphere exposed) surface of an agricultural substrate (as defined hereinabove) or/and immediately surrounding environment of an agricultural substrate, as part of cultivating, breeding, raising, growing, developing, maintaining, or/and storing, the agricultural substrate.

A first main category of agrochemicals particularly relevant to the field and art of the present invention includes agrochemicals that promote or/and enhance cultivating, breeding, raising, growing, developing, maintaining, or/and storing, of agricultural substrates, in a positive manner (i.e., with respect to the agricultural substrates). Exemplary sub-categories of agrochemicals included in this first main category of agrochemicals are fertilizers, growth stimulators, plant growth regulators (those which 'positively' promote or/and enhance plant growth and development), hormones, synergists, and similar types of agrochemicals, which are applied or dispensed to, or/and upon, the outer surface or/and immediately surrounding environment of plant matter types of an agricultural substrate, as part of cultivating, breeding, raising, growing, developing, maintaining, or/and storing, the plant matter, in a positive manner (i.e. with respect to the plant matter).

A second main category of agrochemicals particularly relevant to the disclosed invention, in some embodiments thereof, includes agrochemicals that promote or/and enhance cultivating, breeding, raising, growing, developing, maintaining, or/and storing, of agricultural substrates, in a negative or inhibitory manner (i.e. against 'enemies' of the agricultural substrates). An exemplary sub-category of agrochemicals in this second main category of agrochemicals is pesticides, which are applied or dispensed to, or/and upon, the outer surface or/and immediately surrounding environment of plant matter or animal matter types of an agricultural substrate, as part of cultivating, breeding, raising, growing, developing, or maintaining, the plant matter or animal matter, in a negative or inhibitory manner (i.e., against enemy 'pests' of the plant matter or animal matter).

A pesticide, as an important exemplary sub-category of agrochemicals, is commonly known as generally being any chemical that is used to kill pests, such as insects, and rodents. Herein, in a more encompassing and general manner, which is particularly relevant to the disclosed compounds, a pest may be considered as essentially any living plant or animal organism, or any microorganism, which interferes with or/and inhibits cultivating, breeding, raising, growing, developing, maintaining, or/and storing, of agricultural substrates (plant matter, animal matter).

Pesticides may be divided and classified into major groups. Major pesticide groups are: acaricides or miticides (lethal to ticks and mites), algicides, antifeedants, avicides (lethal to birds), bactericides, bird repellants, chemosterilants, fungicides, safeners, herbicides, insect attractants, insect repellants, insecticides, mammal repellants, mating disrupters, molluscicides, nematicides, plant activators (activate plant defense mechanisms against pests), plant growth regulators (those which inhibit pest plant growth), rodenticides, synergists, and virucides. This classified list of major pesticides groups represents at least fourteen hundred pesticide compounds. Moreover, each major pesticide group is sub-divided into chemical or other classes.

Catalyst Composition:

According to an aspect of embodiments of the invention there is provided a catalyst composition comprising: one or more Lewis acids selected from the group consisting of: $CuCl_2$, $Sc(OTf)_3$, $Fe(OTf)_3$, $In(OTf)_3$, $BF_3 \cdot OEt_2$, TfOH and $Cu(OTf)_2$; a polar solvent selected from the group consisting of: acetonitrile, nitromethane, and 2,2,2-trifluoroethanol (TFE), or a mixture thereof, and RSH, wherein R is selected from the group consisting of: alkyl, benzyl, alkoxy, aryloxy, carbonyl, carboxy, substituted or non-substituted.

In some embodiments, the Lewis acid is in a molar concentration of at least 1.

In some embodiments, the polar solvent is TFE.

It will be recognized that these embodiments are susceptible to various modifications and alternative forms well known to those of skill in the art.

The term "molar concentration" as used herein, may refer to a concentration in units of mol/L at a temperature of approximately 25° C.

General:

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the terms "method" or "process", which are used hereinthroughout interchangeably, refer to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements. The invention is capable of other embodiments or of being practiced or carried out in various ways.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find support in the following examples.

EXAMPLES

Reference is now made to the following examples, which together with the above descriptions illustrate some embodiments of the invention in a non limiting fashion.

Materials and Methods:

All reagents were of reagent grade quality, purchased commercially from Sigma-Aldrich, Alfa-Aesar, or Fluka, and used without further purification ($Cu(OTf)_2$ was purchased from stream chemicals. Purification by column chromatography was performed on Merck chromatographic silica gel (40-60 μm). TLC analyses were performed using Merck silica gel glass plates 60 F254. NMR spectra were recorded on Bruker DPX400, or DMX500 instruments; chemical shifts, given in, are relative to $Me_4Si$ as the internal standard or to the residual solvent peak. HR-MS data were obtained using a Thermoscientific LTQU XL Orbitrap HRMS equipped with APCI (atmospheric-pressure chemical ionization). Gas chromatography data were obtained using an Agilent 7820A GC equipped with FID detector working under standard conditions and an Agilent HP-5 column. HPLC analysis was carried out on an Agilent 1260 instrument equipped with a G4212-60008 photodiode array detector, ES-MS Advion Expression unit and a Agilent reverse phase ZORBAX Eclipse plus C18 3.5 μm column (4.6×100 mm).

Figure 1B:
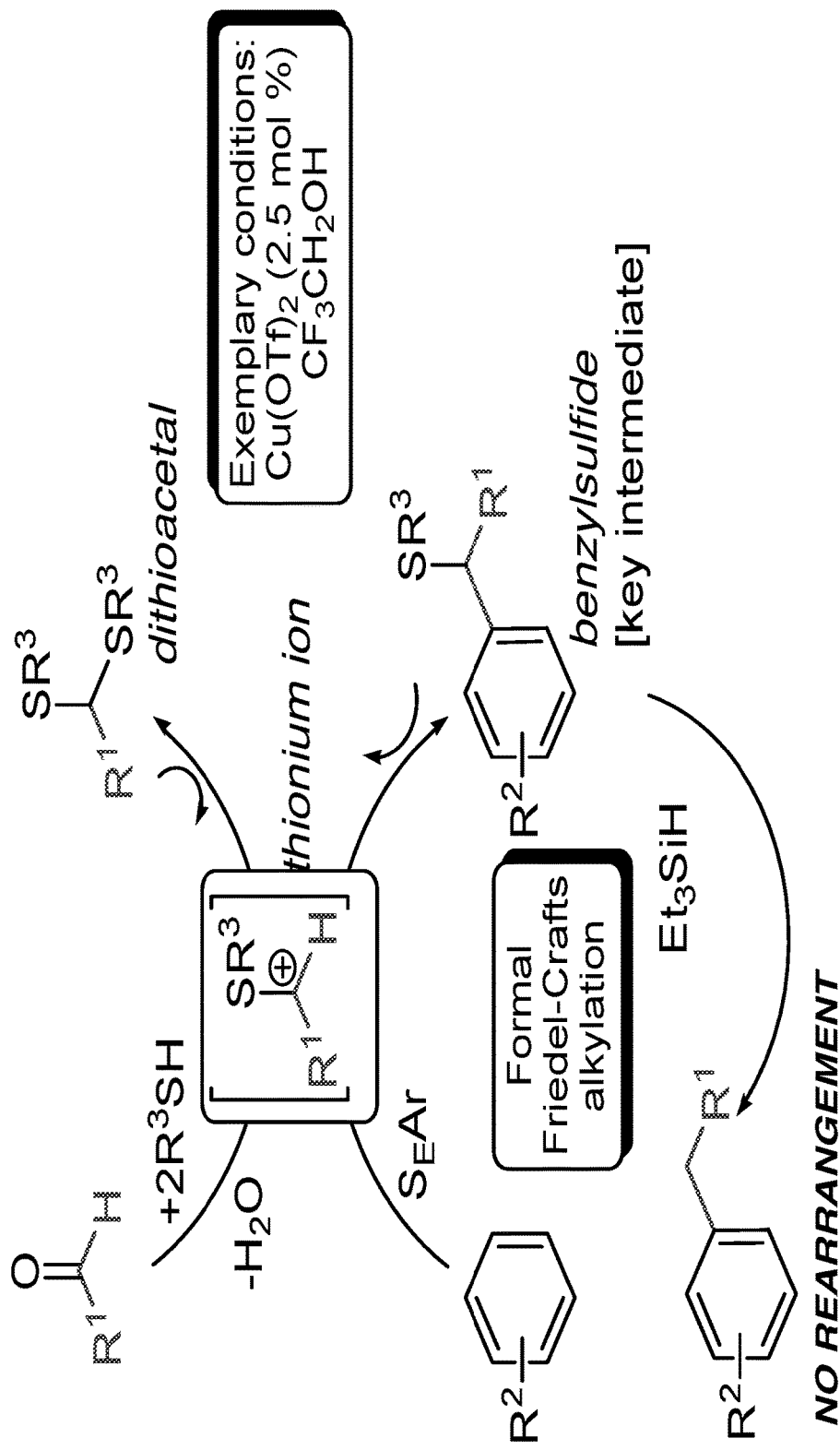

General Synthesis Route:

The synthesis route of the present invention is shown in scheme 1B (FIG. 1B).

Without being bound by any particular theory or mechanism, it is proposed that the mechanism of the synthesis is as exemplified in scheme 1 B (shown in FIG. 1B): in the first step (referred to as "Process A" hereinbelow) an aldehyde is reacted with ethyl thiol in the presence of affordable acid e.g., Lewis acids (such as: $Cu(OTf)_2$), to generate di-thioacetal which is transformed to the active electrophilic species-thionium ion. When the arene is introduced it reacts to thereby generate new carbon-carbon bond. In this process the alkyl scaffold is not harmed and remains in its original structure.

Later the sulfide can be reduced with $Et_3SiH$ as reducing agent in highly selective manner (referred to as "Process B" hereinbelow).

FIG. 1A presents Scheme 1A showing a classic Friedel-Craft alkylation.

FIG. 1B presents, without being bound by any particular theory or mechanism, Scheme 1B showing the process of the present invention, in some embodiments thereof.

Example 1

Process A: Reaction of Aldehyde, Arene and Thiol

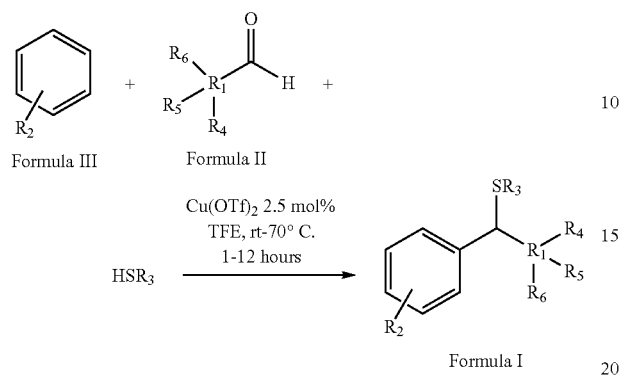

In exemplary procedures, the benzylation of electron rich arenes with benzaldehydes of different electronic natures can be carried out in the presence of different thiols.

Electron deficient aldehydes are more reactive than electron rich aldehydes, while the reaction of benzaldehyde with 2,6-dimethylphenol using thioacetic acid as the promoter reached completion within minutes at room temperature affording obtaining product A1 in 98% yields.

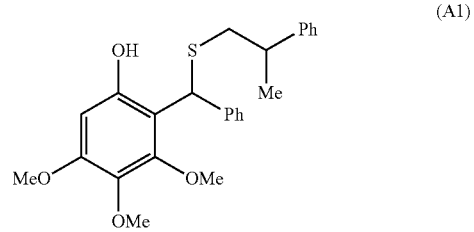 [SMILES: COc1cc(O)c(C(SCC(C)c2ccccc2)c2ccccc2)c(OC)c1OC]
(A1)

Polar functional groups, such as, —OH, —OMe, —$CO_2H$, —CN, —SMe, —Br and —$NMe_2$ are robust under the reaction conditions. The reaction is highly efficient for both linear and branched aliphatic aldehydes, affording benzylsulfides such as A2:

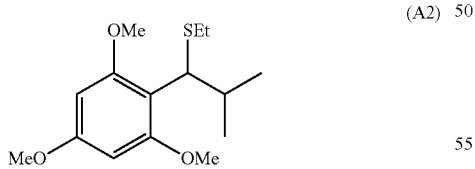
(A2)

in moderate to high yields (up to 92% yield).

Surprisingly, under the reaction conditions, side processes, such as polyalkylation of the aromatic ring or nucleophilic substitution of the benzylsulfide group were not observed. Similar to other electrophilic aromatic substitution reactions, this Pummerer/Friedel-Crafts reaction is reversible; the benzylsulfide products can decompose back to the dithioacetal and the arene coupling partners. This notion can explain the high steric control that was observed in products that were substituted at the less hindered site.

Importantly, tertiary alkylchloride, which are highly reactive in the Friedel-Crafts reaction, are stable under the mild acidic conditions (product A3, 70%) of the reaction. The reaction of e.g., 1,3,5-trimethoxybenzene, with trimethyl orthoformate provided a direct entry to masked aldehyde, A4 in 85%.

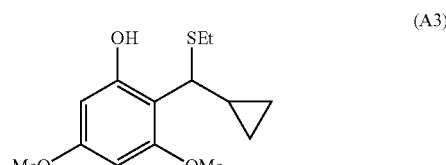
(A3)

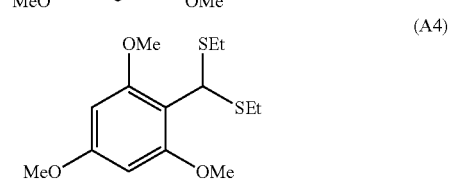
(A4)

In additional exemplary procedures, the suitability of the method for the synthesis of biologically active compounds was evaluated, as well, and the acid-sensitive 17β-estradiol with a secondary alcohol group (A5 70% yield),

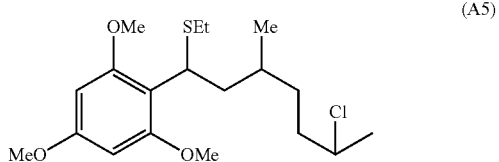
(A5)

the N-Ts protected indole (A6, 98%) and the N-Cbz-protected tyrosine (A7 and A8 in 98% and 41% respectively) were successfully alkylated.

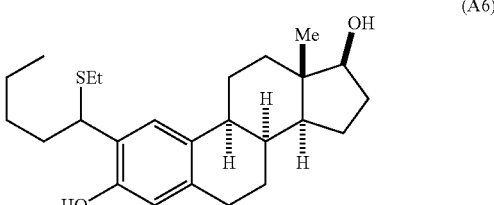
(A6)

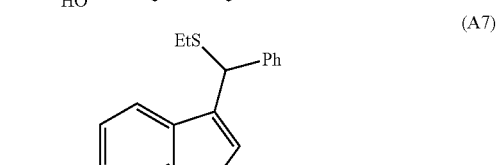
(A7)

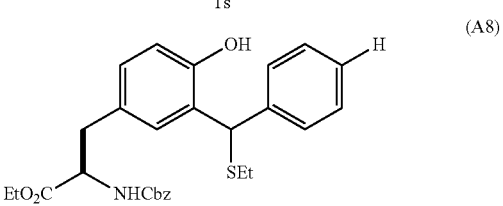
(A8)

Synthesis of Specific Compounds:

In exemplary procedures of process A (also referred to herein as "method A"), a solution of aldehyde (0.75 mmol), arene (0.25 mmol), ethanethiol (1.5 mmol) and Cu(OTf)$_2$ (2.5 mol %) in 2,2,2-trifluoroethanol (0.75 mL), (1.5 mmol) was stirred at the required temperature. Upon completion, all volatiles were removed under reduced pressure and the crude residue purified over silica-gel chromatography affording the desired coupling product.

Compound 3:

4-Anisaldehyde (91 μl, 0.75 mmol), Cu(OTf)$_2$ (2.2 mg, 2.5 mol %), ethanethiol (108 μl, 1 mmol) and anisole (27 μl, 0.25 mmol) were reacted according to method A. The mixture was stirred for 7 h at 50° C. The residual material was purified by column chromatography (silica gel 40-60, hexane/ethyl acetate 98:2) affording compound 3 (39 mg, 54% yield) as a white solid. Characterization data of compound 3: $^1$H NMR (CDCl$_3$/400 MHz): δ 7.34 (d, J=8.6 Hz, 4H), 6.85 (d, J=8.6 Hz, 2H), 5.13 (s, 1H), 3.79 (s, 6H), 2.39 (q, J=7.4 Hz, 2H), 1.22 (t, J=7.4 Hz, 3H); $^{13}$C NMR (CDCl$_3$/100 MHz): δ 158.6, 133.9, 129.3, 113.9, 55.3, 52.4, 26.2, 14.3; HRMS (ESI): m/z calcd for C$_{17}$H$_{20}$O$_2$S [M+Na]$^+$ 311.1076, found 311.1075.

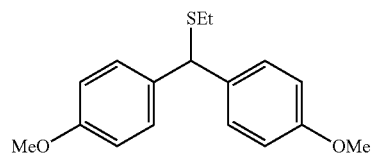

3

Compound 4:

3-Bromobenzaldehyde (92.5 mg, 0.5 mmol), Cu(OTf)$_2$ (2.2 mg, 2.5 mol %), ethanethiol (72 μl, 1 mmol) and anisole (27 μl, 0.25 mmol) were reacted according to method A. The mixture was stirred for 7 h at 50° C. The residual material was purified by column chromatography (silica gel 40-60, hexane/ethyl acetate 97:3) affording compound 4 (59 mg, 70% yield) as white solid. Characterization data of compound 4: $^1$H NMR (CDCl$_3$/400 MHz): δ 7.56 (s, 1H), 7.35 (d, J=8.2 Hz, 2H), 7.30 (d, J=8.6 Hz, 2H), 7.17 (t, J=7.8 Hz, 1H), 6.85 (d, J=8.6 Hz, 2H), 5.09 (s, 1H), 3.79 (s, 3H), 2.39 (q, J=7.4 Hz, 2H), 1.21 (t, J=7.4 Hz, 3H); $^{13}$C NMR (CDCl$_3$/100 MHz): δ 158.8, 144.3, 132.8, 131.3, 130.2, 130.1, 129.3, 126.9, 122.6, 114.0, 55.3, 52.6, 26.3, 14.2; HRMS (ESI): m/z calcd for C$_{16}$H$_{17}$BrOS [M+Na]$^+$ 359.0076 and 361.0055, found 359.0077 and 361.0050.

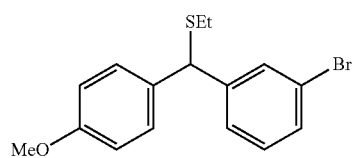

4

Compound 5:

4-Cyanobenzaldehyde (98 mg, 0.75 mmol), Cu(OTf)$_2$ (2.2 mg, 2.5 mol %), ethanethiol (108 μl, 1.5 mmol) and anisole (27 μl, 0.25 mmol) were reacted according to method A. The mixture was stirred for 16 h at 50° C. The residual material was purified by column chromatography (silica gel 40-60, hexane/ethyl acetate 93:7) affording compound 5 (64 mg, 90% yield) as a white solid. Characterization data of compound 5: $^1$H NMR (CDCl$_3$/400 MHz): δ 7.59 (d, J=8.2 Hz, 2H), 7.52 (d, J=8.1 Hz, 2H), 7.29 (d, J=8.7 Hz, 2H), 6.86 (d, J=8.9 Hz, 2H), 5.15 (s, 1H), 3.78 (s, 3H), 2.39 (q, J=7.4 Hz, 2H), 1.21 (t, J 7.4 Hz, 3H); $^{13}$C NMR (CDCl$_3$/100 MHz): δ 159.0, 147.5, 132.4, 132.1, 129.3, 129.0, 118.8, 114.2, 110.8, 55.3, 52.9, 26.3, 14.2; HRMS (ESI): m/z calcd for C$_{17}$H$_{17}$NO$_3$[M+Na]$^+$ 306.1101, found 306.0925.

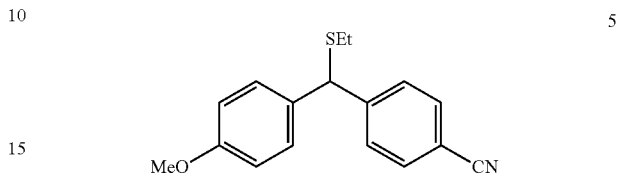

5

Compound 6:

Benzaldehyde (77 μl, 0.75 mmol), Cu(OTf)$_2$ (2.2 mg, 2.5 mol %), ethanethiol (108 μl, 1.5 mmol) and 1,3,5-trimethoxybenzene (42 mg, 0.25 mmol) were reacted according to method A. The mixture was stirred for 4 h at 50° C. The residual material was purified by column chromatography (silica gel 40-60, hexane/ethyl acetate 96:4) affording compound 6 (74 mg, 94% yield) as a thick liquid. Characterization data of compound 6: $^1$H NMR (CDCl$_3$/400 MHz): δ 7.52 (d, J=7.7 Hz, 2H), 7.25 (t, J=7.7 Hz, 2H), 7.15 (t, J=7.3 Hz, 1H), 6.13 (s, 2H), 5.70 (s, 1H), 3.79 (s, 3H), 3.76 (s, 6H), 2.65-2.52 (m, 2H), 1.28 (t, J=7.3 Hz, 3H); $^{13}$C NMR (CDCl$_3$/100 MHz): δ 160.3, 158.5, 142.9, 128.0, 127.6, 125.9, 112.8, 91.4, 55.9, 55.3, 43.3, 27.4, 14.8; HRMS (ESI): m/z calcd for C$_{18}$H$_{22}$O$_3$S [M+Na]$^+$ 341.1182, found 341.1182.

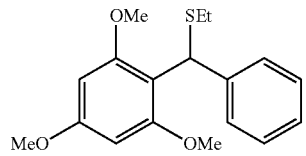

6

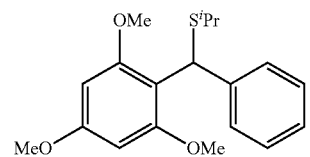

Compound 7:

Benzaldehyde (77 μl, 0.75 mmol), Cu(OTf)$_2$ (2.2 mg, 2.5 mol %), isopropyl thiol (140 μl, 1.5 mmol) and 1,3,5-trimethoxybenzene (42 mg, 0.25 mmol) were reacted according to method A. The mixture was stirred for 6.5 h at 50° C. The residual material was purified by column chromatography (silica gel 40-60, hexane/ethyl acetate 94:6) affording compound 7 (77 mg, 92% yield) as colorless crystals. Characterization data of compound 7: $^1$H NMR (CDCl$_3$/400 MHz): δ 7.60-7.55 (m, 2H), 7.25 (t, J=7.8 Hz, 2H), 7.15 (t, J=7.1 Hz, 1H), 6.14 (s, 2H), 5.72 (s, 1H), 3.79 (s, 3H), 3.77 (s, 6H), 3.02-2.91 (m, 2H), 1.31 (d, J=6.8, 3H), 1.30 (d, J=6.8, 3H); $^{13}$C NMR (CDCl$_3$/100 MHz): δ 160.2, 158.2, 143.4, 128.2, 128.1, 128.0, 127.7, 127.6, 126.0, 125.8, 113.5, 91.4, 55.9, 55.3, 42.3, 36.6, 23.7, 14.7; HRMS (ESI): m/z calcd for $C_{19}H_{24}O_3S$ [M+Na]$^+$ 355.1338, found 355.1338.

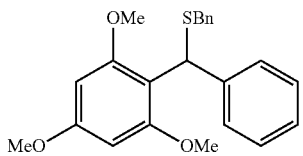

8

Compound 8:

Benzaldehyde (77 µl, 0.75 mmol), Cu(OTf)$_2$ (2.2 mg, 2.5 mol %), benzyl thiol (176 µl, 1.5 mmol) and 1,3,5-trimethoxybenzene (42 mg, 0.25 mmol) were reacted according to method A. The mixture was stirred for 5 h at 50° C. The residual material was purified by column chromatography (silica gel 40-60, hexane/ethyl acetate 94:6) affording compound 8 (62 mg, 65% yield) as pale yellow crystals. Characterization data of compound 8: $^1$H NMR (CDCl$_3$/400 MHz): δ 7.52-7.51 (m, 2H), 7.35-7.21 (m, 8H), 7.19-7.15 (m, 1H), 6.11 (s, 2H), 5.64 (s, 1H), 3.79 (s, 3H), 3.75 (d, J=2.6 Hz, 2H), 3.70 (s, 6H); $^{13}$C NMR (CDCl$_3$/100 MHz): δ 160.3, 158.6, 142.3, 138.9, 129.2, 128.3, 128.1, 127.7, 126.7, 126.0, 112.2, 91.2, 55.8, 55.3, 42.9, 37.6; HRMS (ESI): m/z calcd for $C_{23}H_{24}O_3S$ [M+Na]$^+$ 403.1338, found 403.1337.

Compound 9:

Benzaldehyde (51 mg, 0.5 mmol), Cu(OTf)$_2$ (2.2 mg, 2.5 mol %), 2-phenylpropane-1-thiol (152 mg, 1 mmol) and 3,4,5-trimethoxyphenol (46 mg, 0.25 mmol) were reacted according to method A. The mixture was stirred for 8 h at 50° C. The residual material was purified by column chromatography (silica gel 40-60, hexane/ethyl acetate 93:7) to obtain compound 9 (87 mg, 82% yield) as a thick oil. Characterization data of compound 9: $^1$H NMR (CDCl$_3$/400 MHz): δ 8.19 (s, 1H), 7.37-7.15 (m, 10H), 6.36 (s, 1H), 5.86 (s, 1H), 3.85 (s, 3H), 3.82 (s, 3H), 3.68 (s, 3H), 3.06-2.94 (m, 2H), 2.56 (dd, J=13.3, 9.0 Hz, 2H), 14.1 (d, J=6.9 Hz, 3H); $^{13}$C NMR (CDCl$_3$/100 MHz): δ 153.8, 153.1, 152.4, 145.3, 144.9, 139.2, 139.2, 135.8, 128.6, 128.5, 128.1, 128.0, 127.5, 127.0, 126.7, 126.6, 109.1, 108.8, 97.8, 61.5, 61.0, 55.8, 45.1, 44.3, 40.6, 39.5, 39.0, 21.4, 20.3; HRMS (ESI): m/z calcd for $C_{25}H_{28}O_4S$ [M+Na]$^+$ 447.1601, 447.1593 found 389.1316, 391.1322.

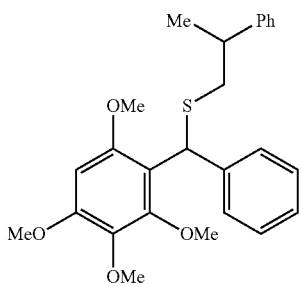

9

Compound 10:

Benzaldehyde (77 µl, 0.75 mmol), Cu(OTf)$_2$ (2.2 mg, 2.5 mol %), thioacetic acid (107 µl, 1.5 mmol) and 2,6-dimethylphenol (30.5 mg, 0.25 mmol) were reacted according to method A. The mixture was stirred for 20 min at room temperature. The residual material was purified by column chromatography (silica gel 40-60, hexane/ethyl acetate 95:5) affording compound 10 (70 mg, 98% yield) as a thick oil. Characterization data of compound 10: $^1$H NMR (CDCl$_3$/400 MHz): δ 7.39-7.35 (m, 4H), 7.27-7.22 (m, 1H), 6.97 (s, 2H), 5.88 (s, 1H), 2.36 (s, 3H), 2.21 (s, 6H); $^{13}$C NMR (CDCl$_3$/100 MHz): δ 194.5, 151.6, 141.5, 132.4, 128.6, 128.5, 128.2, 127.2, 123.3, 51.5, 30.4, 16.1; HRMS (ESI): m/z calcd for $C_{17}H_{18}O_2S$ [M+Na]$^+$ 309.0920 found 309.0918.

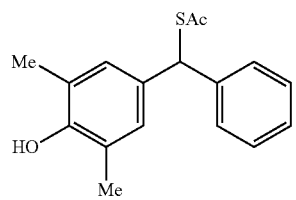

10

Compound 11:

4-Hydroxybeznaldehyde (30.5 mg, 0.25 mmol), Cu(OTf)$_2$ (2.2 mg, 2.5 mol %), ethanethiol (54 µl, 0.75 mmol) and 1,3,5-trimethoxybenzne (54.6 mg, 0.325 mmol) were reacted according to method A. The mixture was stirred for 6 h at 50° C. The residual material was purified by column chromatography (silica gel 40-60, hexane/ethyl acetate 65:35) affording compound 11 (75 mg, 89% yield) as a white solid. Characterization data of compound 11: $^1$H NMR (CDCl$_3$/400 MHz): δ 7.36 (d, J=8.4 Hz, 2H), 6.68 (d, J=8.8 Hz, 2H), 6.12 (s, 2H), 5.63 (s, 1H), 5.39 (br s, OH), 3.78 (s, 3H), 3.75 (s, 6H), 2.61-2.49 (m, 2H), 1.25 (t, J=7.4 Hz, 3H); $^{13}$C NMR (CDCl$_3$/100 MHz): δ 160.1, 158.4, 153.8, 134.9, 129.2, 114.6, 112.8, 91.5, 55.9, 55.4, 42.7, 27.3, 14.7; HRMS (ESI): m/z calcd for $C_{18}H_{22}O_4S$ [M+Na]$^+$ 357.1131, found 357.1129.

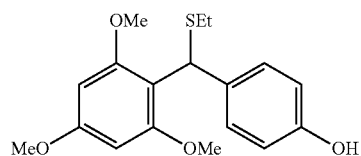

11

Compound 12:

4-Carboxybeznaldehyde (112.5 mg, 0.75 mmol), Cu(OTf)$_2$ (2.2 mg, 2.5 mol %), ethanethiol (108 µl, 1.5 mmol) and 1,3,5-trimethoxybenzne (42 mg, 0.25 mmol) were reacted according to method A. The mixture was stirred for 3 h at 50° C. The residual material was purified by column chromatography (silica gel 40-60, hexane/ethyl acetate 60:40) affording compound 12 (54 mg, 60% yield) as a white solid. Characterization data of compound 12: $^1$H NMR (CDCl$_3$/400 MHz): δ 7.99 (d, J=8.5 Hz, 2H), 7.61 (d, J=8.1 Hz, 2H), 6.10 (s, 2H), 5.70 (s, 1H), 3.79 (s, 3H), 3.74 (s, 6H), 2.64-2.51 (m, 2H), 1.27 (t, J=7.4 Hz, 3H); $^{13}$C NMR (CDCl$_3$/100 MHz): δ 172.3, 160.6, 158.4, 149.6, 129.7, 128.1, 126.8, 111.9, 91.3, 55.8, 55.3, 43.3, 27.4, 14.7; HRMS (ESI): m/z calcd for $C_{19}H_{22}O_5S$ [M+Na]$^+$ 385.1080, found 385.1080.

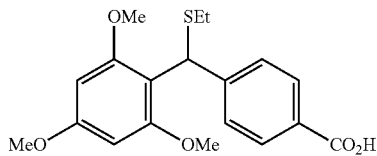

12

Compound 13:

3-Hydroxybenzaldehyde (91.5 mg, 0.75 mmol), Cu(OTf)$_2$ (2.2 mg, 2.5 mol %), ethanethiol (108 µl, 1.5 mmol) and 1,3,5-triethoxybenzene (52.5 mg, 0.25 mmol). The mixture was stirred for 3 h at 50° C. The residual material was purified by column chromatography (silica gel 40-60, hexane/ethyl acetate 95:5) affording compound 13 (77 mg, 82% yield) as a thick oil. Characterization data of compound 13: $^1$H NMR (CDCl$_3$/400 MHz): δ 7.08-7.07 (m, 3H), 6.62-6.60 (m, 1H), 6.08 (s, 2H), 5.66 (s, 1H), 4.96 (br s, OH), 4.03-3.86 (m, 6H), 2.63-2.50 (m, 2H), 1.39 (t, J=7.0 Hz, 3H), 1.31 (t, J=6.9 Hz, 6H), 1.28 (t, J=7.3 Hz, 3H); $^{13}$C NMR (CDCl$_3$/100 MHz): δ 159.4, 157.6, 155.0, 145.2, 128.6, 120.6, 115.2, 112.8, 112.6, 92.3, 64.1, 63.5, 42.9, 27.2, 14.9, 14.86, 14.8; HRMS (ESI): m/z calcd for C$_{21}$H$_{28}$O$_4$S [M+Na]$^+$ 399.1601, found 399.1588.

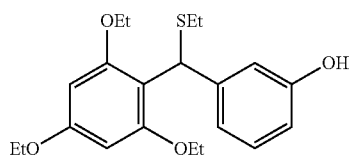

13

Compound 14:

4-Cyanobenzaldehyde (98 mg, 0.75 mmol), Cu(OTf)$_2$ (27 mg, 30 mol %), ethanethiol (108 µl, 1.5 mmol) and mesitylene (35 µl, 0.25 mmol) were reacted according to method A. The mixture was stirred for 16 h at 70° C. The residual material was purified by column chromatography (silica gel 40-60, hexane/diethylether 95:5) affording compound 14 (64 mg, 87% yield) as a white solid. Characterization data of compound 14: $^1$H NMR (CDCl$_3$/400 MHz): δ 7.58-7.56 (m, 2H), 7.53-7.51 (m, 2H), 6.85 (s, 2H), 5.58 (s, 1H), 2.72-2.52 (m, 2H), 2.67 (s, 3H), 2.18 (br s, 6H), 1.30 (t, J=7.4 Hz, 3H); $^{13}$C NMR (CDCl$_3$/100 MHz): δ 147.2, 137.1, 136.6, 135.2, 132.0, 130.4 (br s), 128.6, 126.6, 119.0, 110.1, 48.2, 27.2, 21.1, 20.9, 203, 14.8; HRMS (ESI): m/z calcd for C$_{19}$H$_{21}$NS [M+Na]$^+$ 318.1287, found 318.1285.

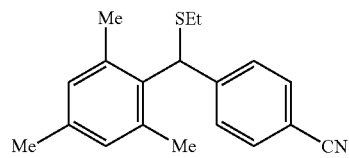

14

Compound 15:

4-Cyanobenzaldehyde (98 mg, 0.75 mmol), Cu(OTf)$_2$ (27 mg, 30 mol %), ethanethiol (108 µl, 1.5 mmol) and thioanisole (38.5 mg, 0.25 mmol) were reacted according to method A. The mixture was stirred for 16 h at 90° C. in sealed tube. The residual material was purified by column chromatography (silica gel 40-60, hexane/diethylether 90:10) affording compound 15 (60 mg, 80% yield) as a white solid. Characterization data of compound 15: $^1$H NMR (CDCl$_3$/400 MHz): δ 7.59 (d, J=8.3 Hz, 2H), 7.51 (d, J=8.3 Hz, 2H), 7.29 (d, J=8.4 Hz, 2H), 7.20 (d, J=8.4 Hz, 2H), 5.15 (s, 1H), 2.45 (s, 3H), 2.40 (q, J=7.4, 2H), 1.21 (t, J=7.4, 3H); $^{13}$C NMR (CDCl$_3$/100 MHz): δ 147.1, 138.1, 136.8, 132.4, 129.1, 128.7, 126.7, 118.7, 111.0, 53.0, 26.4, 15.7, 14.2; HRMS (ESI): m/z calcd for C$_{17}$H$_{17}$NS$_2$ [M+Na]$^+$ 322.0695, found 322.0699.

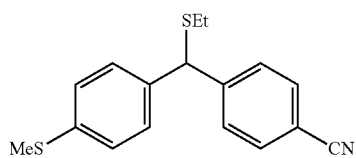

15

Compound 16:

Methyl 4-formylbenzoate (123 mg, 0.75 mmol), Cu(OTf)$_2$ (4.5 mg, 5 mol %), ethanethiol (108 µl, 1.5 mmol) and 1,4-dimethoxybenzene (38.5 mg, 0.25 mmol) were reacted according to method A. The mixture was stirred for 7 h at 70° C. in sealed tube. The residual material was purified by column chromatography (silica gel 40-60, hexane/ethyl acetate 95:5) affording compound 16 (32 mg, 36% yield) as a white solid. Characterization data of compound 16: $^1$H NMR (CDCl$_3$/400 MHz): δ 7.95 (d, J=7.9 Hz, 2H), 7.50 (d, J=7.9 Hz, 2H), 7.19 (s, 1H), 6.80-6.71 (m, 2H), 5.67 (s, 1H), 3.88 (s, 3H), 3.76 (s, 3H), 3.74 (s, 3H), 2.43 (q, J=7.3, 2H), 1.22 (t, J=7.3, 3H); $^{13}$C NMR (CDCl$_3$/100 MHz): δ 167.0, 153.8, 150.9, 147.1, 130.4, 129.7, 128.6, 128.4, 115.2, 112.6, 111.9, 56.3, 55.7, 52.0, 45.9, 26.4, 14.3; HRMS (ESI): m/z calcd for C$_{19}$H$_{22}$O$_4$S [M+Na]$^+$ 369.1131, found 369.1128.

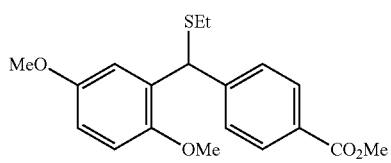

16

Compound 18:

Benzaldehyde (77 µl, 0.75 mmol), Cu(OTf)$_2$ (27 mg, 30 mol %), ethanethiol (108 µl, 1.5 mmol) and protected tyrosine (85.7 mg, 0.25 mmol) were reacted according to method A. The mixture was stirred for 10 h at 70° C. The residual material was purified by column chromatography (silica gel 40-60, hexane/ethyl acetate 70:30) affording compound 18 (51 mg, 41% yield) as a thick oil. Characterization data of compound 18: $^1$H NMR (CDCl$_3$/400 MHz): δ 7.37-7.22 (m, 10H), 6.93 (dt, J=8.1, 2.5 Hz, 1H), 6.84-6.78 (m, 2H), 5.31 (d, J=7.1 Hz, 1H), 5.22-5.16 (m, 1H), 5.07 (d, J=4.1 Hz, 2H), 4.59-4.52 (m, 1H), 4.11-3.92 (m, 2H), 3.04-2.94 (m, 2H), 2.43 (q, J=7.2 Hz, 2H), 1.22 (t, J=7.3 Hz, 3H), 1.16 (t, J=6.9 Hz, 3H); $^{13}$C NMR (CDCl$_3$/100 MHz): δ 171.5, 155.6, 154.3, 139.1, 136.3, 133.6, 131.0, 130.8, 128.7, 128.6, 128.4, 128.3, 128.2, 128.1, 127.5, 125.2, 117.7, 67.0, 61.5, 61.4, 54.8, 50.3, 37.5, 26.3, 14.1; HRMS (ESI): m/z calcd for C$_{28}$H$_{31}$NO$_5$S [M+Na]$^+$ 516.1815 found 516.1943.

Compound 19:

Methyl 4-formylbenzoate (123 mg, 0.75 mmol), Cu(OTf)$_2$ (18 mg, 20 mol %), ethanethiol (108 µl, 1.5 mmol) and protected tyrosine (85.7 mg, 0.25 mmol) were reacted according to method A. The mixture was stirred for 11 h at 70° C. The residual material was purified by column chromatography (silica gel 40-60, hexane/ethyl acetate 70:30) affording compound 19 (51 mg, 37% yield) as a thick oil. Characterization data of compound 19: $^1$H NMR (CDCl$_3$/400 MHz): δ 7.95 (dd, J=4.3, 4.0 Hz, 2H), 7.45 (dd, J=8.0, 2.5 Hz, 2H), 7.35-7.30 (m, 5H), 6.96-6.88 (m, 3H), 6.76-6.68 (m, 1H), 5.43 (s, 1H), 5.25 (d, J=7.1 Hz, 1H), 5.07 (s, 2H), 4.60-4.54 (m, 1H), 4.17-4.00 (m, 2H), 3.88 (s, 3H), 3.04-2.95 (m, 2H), 2.45-2.39 (m, 2H), 1.27-1.16 (m, 6H), 2.16-2.07 (m, 1H), 1.01 (d, J=6.6 Hz, 3H), 0.75 (d, J=6.7 Hz, 3H); $^{13}$C NMR (CDCl$_3$/100 MHz): δ 159.7, 158.9, 139.5, 113.7, 113.4, 91.2, 90.7, 56.1, 55.1, 42.4, 35.7, 30.8, 21.9; HRMS (ESI): m/z calcd for C$_{30}$H$_{33}$NO$_7$S [M+Na]$^+$ 574.1870 found 574.1861.

Compound 20:

Benzaldehyde (77 µl, 0.75 mmol), Cu(OTf)$_2$ (2.2 mg, 2.5 mol %), ethanethiol (108 µl, 1.5 mmol) and 1H-Indole, 1-[(4-methylphenyl)sulfonyl]-(67.25 mg, 0.25 mmol) were reacted according to method A. The mixture was stirred for 4 h at 50° C. The residual material was purified by column chromatography (silica gel 40-60, hexane/ethyl acetate 93:7) affording compound 20 (104 mg, 98% yield) as a thick yellowish oil. Characterization data of compound 20: $^1$H NMR (CDCl$_3$/400 MHz): δ 8.00 (d, J=8.2 Hz, 1H), 7.78 (d, J=7.9 Hz, 2H), 7.60 (s, 1H), 7.49 (d, J=7.9 Hz, 1H), 7.42 (d, J=8.2 Hz, 2H), 7.35-7.26 (m, 4H), 7.24 (d, J=8.4 Hz, 2H), 7.19 (t, J=7.6 Hz, 1H), 5.31 (s, 1H), 2.50-2.43 (m, 2H), 2.37 (s, 3H), 1.25 (t, J=7.4 Hz, 3H); $^{13}$C NMR (CDCl$_3$/100 MHz): δ 145.0, 140.2, 135.7, 135.1, 129.9, 129.7, 128.6, 128.2, 127.5, 126.9, 126.8, 125.0, 124.9, 123.4, 123.2, 120.5, 113.9, 45.2, 26.2, 21.6, 14.4; HRMS (ESI): m/z calcd for C$_{24}$H$_{23}$NO$_2$S$_2$ [M+Na]$^+$ 444.1062 found 444.1067.

Compound 21:

Isobutyrlaldehyde (68.4 µl, 0.75 mmol), Cu(OTf)$_2$ (2.2 mg, 2.5 mol %), ethanethiol (108 µl, 1.5 mmol) and 2-naphthol (36 mg, 0.25 mmol) were reacted according to method A. The mixture was stirred for 4 h at 50° C. The residual material was purified by column chromatography (silica gel 40-60, hexane/diethylether 98:2) affording compound 21 (57 mg, 87% yield) as a thick oil. Characterization data of compound 21: $^1$H NMR (CDCl$_3$/400 MHz): δ 8.72 (s, OH), 7.93 (d, J=8.7 Hz, 1H), 7.78 (d, J=8.0 Hz, 1H), 7.72 (d, J=8.9 Hz, 1H), 7.47 (ddd, J=1.4, 6.8, 9.0 Hz, 1H), 7.33 (ddd, J=0.9, 6.7, 8.8 Hz, 1H), 7.15 (d, J=8.8 Hz, 1H), 4.84 (d, J=8.7 Hz, 1H), 2.46-2.37 (m, 1H), 2.32-2.26 (m, 2H), 1.22 (t, J=6.6 Hz, 3H), 1.12 (t, J=7.4 Hz, 3H), 0.84 (t, J=6.7 Hz, 3H); $^{13}$C NMR (CDCl$_3$/100 MHz): δ 154.5, 134.0, 129.5, 129.1, 126.7, 122.9, 122.0, 120.2, 116.0, 49.7, 32.6, 25.0, 21.9, 21.3, 14.6; HRMS (ESI): m/z calcd for C$_{16}$H$_{20}$OS [M+Na]$^+$ 283.1127, found 283.1066.

Compound 22:

Isobutyrlaldehyde (68.4 µl, 0.75 mmol), Cu(OTf)$_2$ (2.2 mg, 2.5 mol %), ethanethiol (108 µl, 1.5 mmol) and 6-bromo-2-naphthol (55.7 mg, 0.25 mmol) were reacted according to method A. The mixture was stirred for 12 h at 50° C. The residual material was purified by column chromatography (silica gel 40-60, hexane/diethylether 98:2) affording compound 22 (82 mg, 97% yield) as a thick oil. Characterization data of compound 22: $^1$H NMR (CDCl₃/400 MHz): δ 8.70 (s, OH), 7.9 (d, J=2.2 Hz, 1H), 7.8 (d, J=9.3 Hz, 1H), 7.6 (d, J=8.8 Hz, 1H), 7.5 (dd, J=2.2, 9 Hz, 1H), 7.15 (d, J=8.8 Hz, 1H), 4.73 (d, J=8.7 Hz, 1H), 2.41-2.3 (m, 1H), 2.26 (q, J=7.3 Hz, 2H), 1.2 (t, J=6.5 Hz, 3H), 1.1 (t, J=7.4 Hz, 3H), 0.8 (t, J=6.7 Hz, 3H); $^{13}$C NMR (CDCl₃/100 MHz): δ 154.7, 132.6, 130.9, 130.3, 129.8, 128.6, 123.8, 121.3, 116.49, 116.41, 49.6, 32.5, 25.0, 21.9, 21.3, 14.6; HRMS (ESI): m/z calcd for $C_{16}H_{19}BrOS$ [M+Na]⁺ 361.0232 and 363.0212, found 361.0242 and 363.0218.

Compound 23:

Isobutyrlaldehyde (68 μl, 0.75 mmol), Cu(OTf)₂ (2.2 mg, 2.5 mol %), ethanethiol (108 μl, 1.5 mmol) and trimethoxybenzene (42 mg, 0.25 mmol) were reacted according to method A. The mixture was stirred for 2 h at 50° C. in sealed tube. The residual material was purified by column chromatography (silica gel 40-60, hexane/ethyl acetate 96:4) affording compound 23 (60 mg, 85% yield) as a thick oil. Characterization data of compound 23: ¹H NMR (CDCl₃/400 MHz): δ 6.12 (s, 1H), 6.10 (s, 1H), 3.93 (d, J=10.5 Hz, 1H), 3.80 (s, 3H), 3.79 (s, 3H), 3.77 (s, 3H), 2.50-2.35 (m, 3H), 1.19 (d, J=6.7 Hz, 3H), 1.18 (t, J=7.8 Hz, 3H), 0.67 (d, J=6.7 Hz, 3H); ¹³C NMR (CDCl₃/100 MHz): δ 159.6, 159.5, 157.8, 113.0, 91.7, 90.3, 55.9, 55.7, 55.2, 47.8, 31.8, 27.3, 22.5, 21.4, 15.1; HRMS (ESI): m/z calcd for $C_{15}H_{24}O_3S$ [M+Na]⁺ 307.1338, found 307.1337.

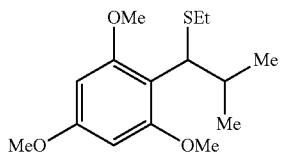

23

Compound 24:

Isobutyrlaldehyde (68.4 μl, 0.75 mmol), Cu(OTf)₂ (2.2 mg, 2.5 mol %), ethanethiol (108 μl, 1.5 mmol) and 3,4,5-trimethoxyphenol (46 mg, 0.25 mmol) were reacted according to method A. The mixture was stirred for 4.5 h at 50° C. The residual material was purified by column chromatography (silica gel 40-60, hexane/ethyl acetate 95:5) affording compound 24 (62 mg, 82% yield) as a white solid. Characterization data of compound 24: ¹H NMR (CDCl₃/400 MHz): δ 7.92 (s, OH), 6.22 (s. 1H), 4.27 (d, J=9.2 Hz, 1H), 3.86 (s, 3H), 3.79 (s, 3H), 3.75 (s, 3H), 2.37-2.23 (m, 2H), 2.16-2.07 (m, 1H), 1.14 (t, J=7.4 Hz, 3H), 1.10 (d, J=6.7 Hz, 3H), 0.81 (d, J=6.7 Hz, 3H); ¹³C NMR (CDCl₃/100 MHz): δ 153.0, 152.5, 152.3, 135.3, 110.4, 97.3, 61.0, 60.8, 55.7, 48.2, 32.3, 25.1, 21.7, 21.4, 14.3; HRMS (ESI): m/z calcd for $C_{15}H_{24}O_4S$ [M+Na]⁺ 323.1288, found 323.1286.

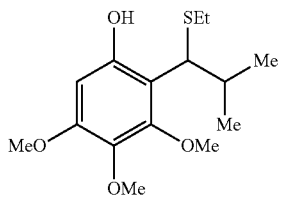

24

Compound 25:

Isovaleraldehyde (68.4 μl), Cu(OTf)₂ (2.2 mg, 2.5 mol %), ethanethiol (108 μl, 1.5 mmol) and 3,4,5-trimethoxyphenol (46 mg). The mixture was stirred for 4 h at 50° C. The residual material was purified by column chromatography (silica gel 40-60, hexane/ethyl acetate 95:5) affording compound 25 (56 mg, 72% yield) as a thick oil. Characterization data of compound 25: ¹H NMR (CDCl₃/400 MHz): δ 7.85 (s, OH), 6.24 (s. 1H), 4.65 (t, J=7.5 Hz, 1H), 3.86 (s, 3H), 3.79 (s, 3H), 3.76 (s, 3H), 2.40-2.25 (m, 2H), 1.73-1.58 (m, 3H), 1.17 (t, J=7.4 Hz, 3H), 0.92 (d, J=7.3 Hz, 3H), 0.89 (d, J=7.3 Hz, 3H); ¹³C NMR (CDCl₃/100 MHz): δ 153.0, 152.5, 152.0, 135.4, 111.3, 97.6, 61.2, 60.9, 55.7, 43.1, 38.4, 26.2, 25.0, 22.7, 22.1, 14.3; HRMS (ESI): m/z calcd for $C_{16}H_{26}O_4S$ [M+Na]⁺ 337.1444, found 337.1441.

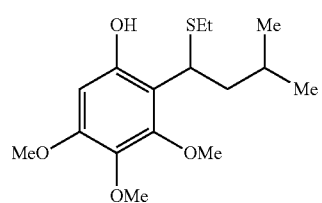

25

Compound 26:

Trimethylacetaldehyde (81 μl, 0.75 mmol), Cu(OTf)₂ (2.2 mg, 2.5 mol %), ethanethiol (108 μl, 1.5 mmol) and 3,5-dimethoxyphenol (38.5 mg, 0.25 mmol) were reacted according to method A. The mixture was stirred for 16 h at 70° C. The residual material was purified by column chromatography (silica gel 40-60, hexane/diethylether 97:3) affording compound 26 (66 mg, 92% yield) as a white solid. Characterization data of compound 26: ¹H NMR (CDCl₃/400 MHz): δ 8.79 (s, OH), 6.07 (d, J=2.4 Hz, 1H), 6.03 (d, J=2.5 Hz, 2H), 4.56 (s, 1H), 3.76 (s, 3H), 3.72 (s, 3H), 2.28 (q, J=7.6 Hz, 2H), 1.14 (t, J=7.4 Hz, 3H), 1.01 (s, 9H); ¹³C NMR (CDCl₃/100 MHz): δ 160.1, 159.8, 158.6, 103.8, 94.8, 90.9, 55.5, 55.1, 50.5, 37.5, 28.5, 24.9, 10.1; HRMS (ESI): m/z calcd for $C_{15}H_{24}O_3S$ [M+Na]⁺ 307.1338, found 307.1337.

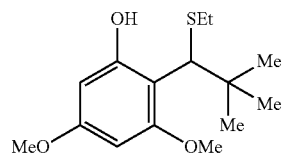

26

Compound 27:

Acetaldehyde (42 μl, 0.75 mmol), Cu(OTf)₂ (2.2 mg, 2.5 mol %), ethanethiol (108 μl, 1.5 mmol) and sesamol (34.5 mg, 0.25 mmol) were reacted according to method A. The mixture was stirred for 1.5 h at 50° C. The residual material was purified by column chromatography (silica gel 40-60, hexane/diethylether 90:10) affording compound 27 (46 mg, 82% yield) as a thick oil. Characterization data of compound 27: ¹H NMR (CDCl₃/400 MHz): δ 7.13 (br s, OH), 6.57 (s, 1H), 6.45 (s, 1H), 5.88 (s, 1H), 5.88 (s, 1H), 4.06 (q, J=7.1 Hz, 1H), 2.39 (q, J=7.3 Hz, 2H), 1.57 (d, J=7.1 Hz, 3H), 1.19 (t, J=7.3 Hz, 3H); ¹³C NMR (CDCl₃/100 MHz): δ 150.2, 147.5, 141.2, 118.7, 108.0, 101.1, 100.0, 41.7, 24.9, 20.4, 14.4; HRMS (ESI): m/z calcd for $C_{11}H_{14}O_3S$ [M+Na]⁺ 249.0556, found 249.0547.

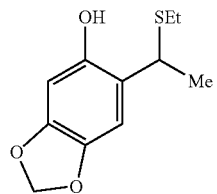

27

Compound 28:

Valeraldehyde (75 μl, 0.75 mmol), Cu(OTf)$_2$ (2.2 mg, 2.5 mol %), ethanethiol (108 μl, 1.5 mmol) and 2,6-dimethylphenol (30.5 mg, 0.25 mmol) were reacted according to method A. The mixture was stirred for 3 h at 50° C. The residual material was purified by column chromatography (silica gel 40-60, hexane/diethylether 93:7) affording compound 28 (47 mg, 74% yield) as a colorless oil. Characterization data of compound 28: $^1$H NMR (CDCl$_3$/400 MHz): δ 6.90 (s, 2H), 3.66 (dd, J=8.6, 6.3 Hz, 1H), 2.35-2.25 (m, 2H), 2.23 (s, 3H), 1.87-1.74 (m, 2H), 1.35-1.25 (m, 4H), 1.16 (t, J=7.4 Hz, 3H), 0.86 (t, J=7.1 Hz, 3H); $^{13}$C NMR (CDCl$_3$/100 MHz): δ 160.0, 134.5, 127.9, 122.8, 48.9, 36.5, 30.0, 25.0, 22.5, 16.1, 14.5, 14.0; HRMS (ESI): m/z calcd for C$_{15}$H$_{24}$OS [M+Na]$^+$ 275.1440 found 275.1434.

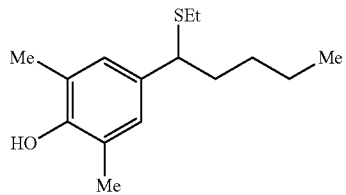

28

Compound 29:

Cyclopropanecarboxyaldehyde (56 μl, 0.75 mmol), Cu(OTf)$_2$ (2.2 mg, 2.5 mol %), ethanethiol (108 μl, 1.5 mmol) and 3,5-dimethoxyphenol (38.5 mg, 0.25 mmol) were reacted according to method A. The mixture was stirred for 16 h at 8° C. The residual material was purified by column chromatography (silica gel 40-60, hexane/ethyl acetate 97:3) affording compound 29 (19 mg, 28% yield) as a thick oil. Characterization data of compound 29: $^1$H NMR (CDCl$_3$/500 MHz): δ 8.34 (s, OH), 6.12 (d, J=2.4 Hz, 1H), 6.06 (d, J=2.4 Hz, 1H), 4.08 (d, J=9.7 Hz, 1H), 3.77 (s, 3H), 3.74 (s, 3H), 2.36-2.25 (m, 2H), 1.31-1.24 (m, 1H), 1.13 (t, J=7.3 Hz, 3H), 0.63-0.58 (m, 1H), 0.46-0.31 (m, 3H); $^{13}$C NMR (CDCl$_3$/125 MHz): δ 160.3, 158.7, 158.1, 105.8, 94.9, 91.3, 55.7, 55.2, 43.9, 24.9, 14.8, 14.3, 5.7, 5.2; HRMS (ESI): m/z calcd for C$_{14}$H$_{20}$O$_3$S [M+H]$^+$ 269.1206, found 269.1211.

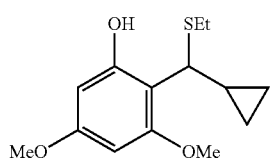

29

Compound 30:

Trimethyl orthoformate (82 μl, 0.75 mmol), Cu(OTf)$_2$ (2.2 mg, 2.5 mol %), ethanethiol (108 μl, 1.5 mmol) and 1,3,5-trimethoxybenzene (42 mg, 0.25 mmol) were reacted according to method A. The mixture was stirred for 6 h at 50° C. The residual material was purified by column chromatography (silica gel 40-60, ethyl acetate/hexane 94:6) affording compound 30 (64 mg, 85% yield) as a thick oil. Characterization data of compound 30: $^1$H NMR (CDCl$_3$/500 MHz): δ 6.13 (s, 1H), 6.07 (s, 1H), 5.40 (s, 1H), 3.86 (s, 3H), 3.79 (s, 3H), 3.78 (s, 3H), 2.60 (q, J=7.4 Hz, 4H), 1.24 (t, J=7.4 Hz, 6H); $^{13}$C NMR (CDCl$_3$/125 MHz): δ 160.5, 160.0, 156.3, 111.2, 92.0, 90.3, 56.0, 55.9, 55.3, 43.4, 27.8, 14.7; HRMS (ESI): m/z calcd for C$_{14}$H$_{22}$O$_3$S$_2$ [M+Na]$^+$ 325.0903 found 325.0906.

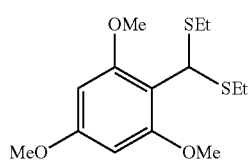

30

Compound 31:

9-bromo-1-nonanal (165 mg, 0.75 mmol), Cu(OTf)$_2$ (2.2 mg, 2.5 mol %), ethanethiol (108 μl, 1.5 mmol) and 3,4,5-trimethoxyphenol (46 mg, 0.25 mmol) were reacted according to method A. The mixture was stirred for 5 h at 50° C. The residual material was purified by column chromatography (silica gel 40-60, hexane/ethyl acetate 92:8) affording compound 31 (87 mg, 77% yield) as a thick oil. Characterization data of compound 31: $^1$H NMR (CDCl$_3$/400 MHz): δ 7.86 (br s, OH), 6.24 (s, 1H), 4.55 (t, J=7.3 Hz, 1H), 3.86 (s, 3H), 3.80 (s, 3H), 3.77 (s, 3H), 3.37 (t, J=6.8 Hz, 2H), 2.41-2.26 (m, 2H), 1.85-1.77 (m, 4H), 1.41-1.20 (m, 10H), 1.17 (t, J=7.4 Hz, 3H); $^{13}$C NMR (CDCl$_3$/100 MHz): δ 155.1, 152.4, 152.17, 135.4, 110.9, 97.5, 61.2, 60.9, 55.7, 40.3, 34.0, 32.8, 29.2, 28.6, 28.1, 27.9, 25.1, 14.3; HRMS (ESI): m/z calcd for C$_{20}$H$_{33}$BrO$_4$S [M+Na]+471.1175 and 473.115, found 471.1167 and 473.1149.

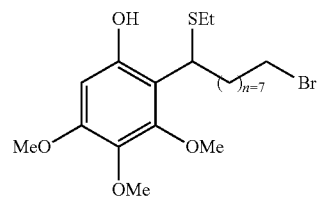

31

Compound 32:

7-chloro-3,7-dimethyloctanal (90 mg, 0.4 mmol), Cu(OTf)$_2$ (2.2 mg, 2.5 mol %), ethanethiol (108 μl, 1.5 mmol) and 1,3,5-trimethoxybenzne (33.6 mg, 0.2 mmol) were reacted according to method A. The mixture was stirred for 0.5 h at 50° C. The residual material was purified by column chromatography (silica gel 40-60, hexane/ethyl acetate 95:5) affording compound 32 (71 mg, 70% yield) as a thick oil. Characterization data of compound 32: $^1$H NMR (CDCl$_3$/500 MHz): δ 6.12 (m, 1H), 6.10 (m, 1H), 4.56-4.47 (m, 1H), 3.82 (s, 3H), 3.79 (s, 6H), 2.53-2.35 (m, 2H), 1.98-1.83 (m, 1H), 1.67-1.58 (m, 2H), 1.53 (s, 3H), 1.52 (s, 3H), 1.42-1.31 (m, 2H), 1.22-1.19 (m, 3H), 1.19-1.04 (m, 2H), 0.84 (t, J=5.5 Hz, 3H); $^{13}$C NMR (CDCl$_3$/125 MHz): δ 160.2, 159.8, 158.2, 111.2, 91.7, 90.3, 71.4, 55.9, 55.7, 55.3, 46.3, 41.2, 37.7, 37.1, 32.5, 31.5, 26.3, 22.6, 19.5, 15.0; HRMS (ESI): m/z calcd for $C_{21}H_{34}O_3S$ [M–(HCl)+Na]$^+$ 389.2121 found 389.2124.

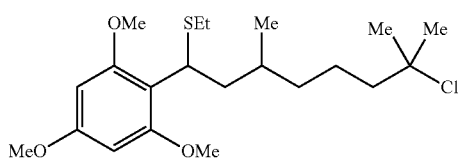

Compound 33:

7-hyroxycitronellal (140 µl, 0.75 mmol), Cu(OTf)$_2$ (2.2 mg, 2.5 mol %), ethanethiol (108 µl, 1.5 mmol) and 1,3,5-trimethoxybenzene (42 mg, 0.25 mmol) were reacted according to method A. The mixture was stirred for 2 h at room temperature. The residual material was purified by column chromatography (silica gel 40-60, hexane/ethyl acetate 80:20) affording compound 33 (68 mg, 71% yield) as a thick oil. Characterization data of compound 33: $^1$H NMR (CDCl$_3$/400 MHz): δ 6.12 (s, 1H), 6.09 (s, 1H), 4.54-4.46 (m, 1H), 3.80 (s, 3H), 3.78 (s, 6H), 2.51-2.32 (m, 3H), 1.96-1.84 (m, 1H), 1.56-1.47 (m, 1H), 1.40-1.32 (m, 4H), 1.24-1.19 (m, 5H), 1.17 (s, 3H), 1.15 (s, 3H), 0.82 (t, J=4.5 Hz, 3H); $^{13}$C NMR (CDCl$_3$/100 MHz): δ 160.2, 159.8, 158.2, 112.4, 111.4, 91.7, 90.3, 71.0, 55.9, 55.7, 55.2, 44.2, 41.3, 38.1, 37.1, 31.4, 29.1, 26.3, 21.6, 20.0, 19.4, 15.0; HRMS (ESI): m/z calcd for $C_{21}H_{36}O_4S$ [M+Na]$^+$ 407.2227 found 407.2218.

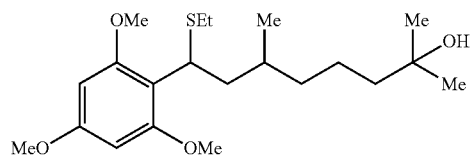

Compound 34:

Glutaraldehyde [25% V/V in H$_2$O] (188 µl, 0.75 mmol), Cu(OTf)$_2$ (9 mg, 10 mol %), ethanethiol (108 µl, 1.5 mmol) and 1,3,5-trimethoxybenzene (42 mg, 0.25 mmol) were reacted according to method A. The mixture was stirred for 8 h at 50° C. The residual material was purified by column chromatography (silica gel 40-60, hexane/ethyl acetate 95:5) affording compound 34 (61 mg, 58% yield) as a thick oil. Characterization data of compound 34: $^1$H NMR (CDCl$_3$/400 MHz): δ 6.11 (s, 1H), 6.09 (s, 1H), 4.36 (dd, J=9.2, 6.7 Hz, 1H), 3.80 (s, 3H), 3.78 (s, 6H), 3.69 (t, J=7.1 Hz, 1H), 2.66-2.39 (m, 6H), 2.15-2.08 (m, 1H), 1.95-1.88 (m, 1H), 1.82-1.67 (m, 2H), 1.54-1.47 (m, 1H), 1.45-1.38 (m, 1H), 1.21 (t, J=7.5 Hz, 3H), 1.19 (t, J=7.5 Hz, 6H); $^{13}$C NMR (CDCl$_3$/100 MHz): δ 160.0, 159.8, 157.9, 111.7, 91.7, 90.3, 55.9, 55.7, 55.3, 51.2, 39.0, 35.7, 33.9, 26.6, 26.2, 24.1, 23.9, 15.1, 14.6, 14.5; HRMS (ESI): m/z calcd for $C_{20}H_{34}O_3S_3$ [M+Na]$^+$ 441.1562 found 441.1558.

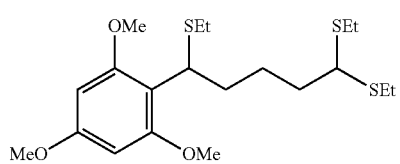

Compound 35:

Compound 34 (40.8 mg, 0.1 mmol) was treated with Cu(OTf)$_2$ (0.8 mg, 2.5 mol %) and Et$_3$SiH at room temperature in 2,2,2-trifluoroethanol (0.3 ml). The mixture was stirred for 4 h at 50° C. The residual material was purified by column chromatography (silica gel 40-60, hexane/ethyl acetate 96:4) affording compound 35 (25 mg, 70% yield) as a thick oil. Characterization data of compound 35: $^1$H NMR (CDCl$_3$/500 MHz): δ 6.12 (s, 2H), 3.80 (s, 3H), 3.79 (s, 6H), 2.71-2.65 (m, 2H), 2.62-2.54 (m, 4H), 2.55 (t, J=7.2 Hz, 1H), 1.83 (q, J=7.4 Hz, 2H), 1.59-1.53 (m, 2H), 1.48-1.42 (m, 2H), 1.25 (t, J=7.4 Hz, 3H); $^{13}$C NMR (CDCl$_3$/125 MHz): δ 159.1, 158.8, 111.6, 90.5, 55.7, 55.3, 51.4, 36.0, 31.6, 28.9, 27.6, 24.2, 22.7, 22.3, 14.6, 14.1; HRMS (ESI): m/z calcd for $C_{18}H_{30}O_3S_2$ [M+Na]$^+$ 381.1529, found 381.1526.

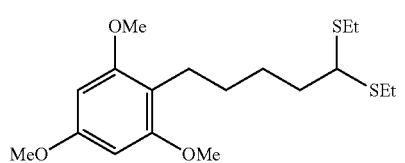

Example 2

Process B; Reduction of the Thiol

An exemplary embodiment of the process of the invention is shown in the following equation:

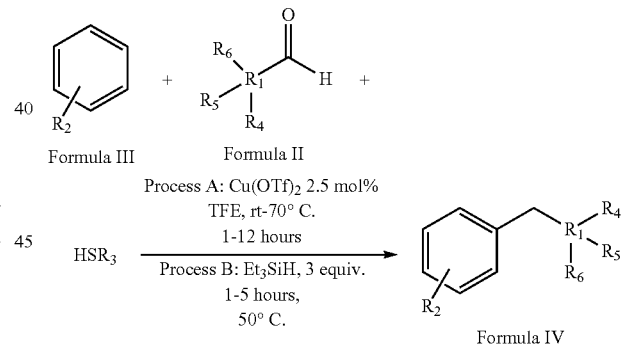

In Process B (also referred to as: "Method B") the products obtained according by process A were reduced by Et$_3$SiH as described hereinbelow, to thereby form a compound represented by Formula IV, as defined hereinabove.

Synthesis of Specific Compounds:

In exemplary procedures, "process A" was first performed, i.e. a solution of aldehyde (0.75 mmol), arene (0.25 mmol), ethanethiol (1.5 mmol) and Cu(OTf)$_2$ (2.5 mol %) in 2,2,2-trifluoroethanol (0.75 mL), (1.5 mmol) was stirred at the required temperature.

Upon completion, the reaction mixture was cooled to room temperature and triethylsilane (0.75 mmol) was added and the reaction was stirred at 50° C. At the end of the reduction process, all volatiles were removed under reduced pressure and the crude residue purified over silica-gel chromatography affording the desired coupling product.

Compound 36:

Paraformaldehyde (22.5 mg, 0.75 mmol), Cu(OTf)$_2$ (2.2 mg, 2.5 mol %), ethanethiol (108 µl, 1.5 mmol) and 3,5-dimethoxyphenol (39 mg, 0.25 mmol) were reacted according to method B. The mixture was stirred for 7 h at 50° C. in sealed tube. After the addition of Et$_3$SiH (119 µl, 0.75 mmol) the reaction was stirred for 4 h at 50° C. The residual material was purified by column chromatography (silica gel 40-60, hexane/ethyl acetate 90:10) affording compound 36 (21.3 mg, 51% yield) as a white solid. Characterization data of compound 36: $^1$H NMR (CDCl$_3$/400 MHz): δ 6.10 (s, 1H), 6.05 (s, 1H), 3.79 (s, 3H), 3.75 (s, 3H), 2.04 (s, 3H); $^{13}$C NMR (CDCl$_3$/100 MHz): δ 159.9, 159.1, 155.6, 106.9, 93.2, 91.3, 55.2, 35.6, 33.5, 29.8; HRMS (ESI): m/z calcd for C$_9$H$_{12}$O$_3$[M+H]$^+$ 169.0859, found 169.0858.

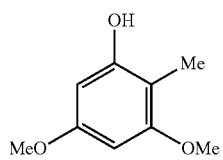

36

Compound 37:

Acetaldehyde (42 µl, 0.75 mmol), Cu(OTf)$_2$ (2.2 mg, 2.5 mol %), ethanethiol (108 µl, 1.5 mmol) and sesamol (34.5 mg, 0.25 mmol) were reacted according to method B. After the addition of Et$_3$SiH (116 µl, 0.75 mmol) the reaction was stirred for 1.5 h at 50° C. The residual material was purified by column chromatography (silica gel 40-60, hexane/ethyl acetate 90:10) affording compound 37 (34 mg, 81% yield) as a thick oil. Characterization data of compound 37: $^1$H NMR (CDCl$_3$/400 MHz): δ 6.62 (s, 1H), 6.39 (s, 1H), 5.87 (s, 2H), 4.85 (br s, OH), 2.54 (q, J=7.5 Hz, 2H), 1.19 (t, J=7.5 Hz, 3H); $^{13}$C NMR (CDCl$_3$/100 MHz): δ 147.6, 145.8, 141.4, 121.9, 108.6, 100.9, 98.1, 22.8, 14.4; HRMS (ESI): m/z calcd for C$_9$H$_{10}$O$_3$[M+H]$^+$ 167.0703, found 167.0706.

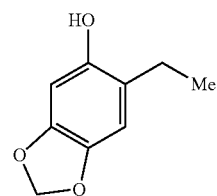

37

Compound 38:

Isobutyrlaldehyde (46 µl, 0.75 mmol), Cu(OTf)$_2$ (2.2 mg, 2.5 mol %), ethanethiol (108 µl, 1.5 mmol) and 3,5-dimethylphenol (30.5 mg, 0.25 mmol) were reacted according to method B. The mixture was stirred for 6 h at 50° C. After the addition of Et$_3$SiH (116 µl, 0.75 mmol) the reaction was stirred for 3 h at 50° C. The residual material was purified by column chromatography (silica gel 40-60, hexane/diethylether 96:4) affording compound 38 (33 mg, 73% yield) as a colorless thick oil. Characterization data of compound 38: $^1$H NMR (CDCl$_3$/400 MHz): δ 6.6 (s, 1H), 6.46 (s, 1H), 4.6 (s, OH), 2.5 (d, J=7.3 Hz, 2H), 2.3 (s, 3H), 2.2 (s, 3H), 1.9 (non, J=6.8 Hz, 1H), 0.96 (d, J=6.6 Hz, 6H); $^{13}$C NMR (CDCl$_3$/100 MHz): δ 153.8, 138.1, 136.1, 123.7, 123.3, 113.7, 35.0, 28.9, 22.7, 20.9, 19.9; HRMS (ESI): m/z calcd for C$_{12}$H$_{18}$O [M+H]$^+$ 179.1430, found 179.1429.

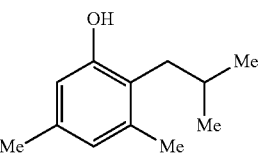

38

Compound 39-d$_1$:

Isobutyrlaldehyde (68 µl, 0.75 mmol), Cu(OTf)$_2$ (2.2 mg, 2.5 mol %), ethanethiol (108 µl, 1.5 mmol) and 2,6-dimethylphenol (30.5 mg, 0.25 mmol) were reacted according to method B. The mixture was stirred for 4 h at 50° C. After the addition of Et$_3$SiH (119 µl, 0.75 mmol) the reaction was stirred for 4 h at 50° C. The residual material was purified by column chromatography (silica gel 40-60, hexane/ethyl acetate 96:4) affording compound 39-d$_1$ (32 mg, 71% yield) as thick yellowish oil. Characterization data of compound 39-d$_1$: $^1$H NMR (CDCl$_3$/500 MHz): δ 6.75 (s, 2H), 2.32 (d, J=7.1 Hz, 1H), 2.23 (s, 6H), 1.78 (oct, J=6.6 Hz, 1H), 0.89 (d, J=6.6 Hz, 6H), 2.39-2.27 (m, 3H), 2.19-2.08 (m, 2H), 1.96-1.93 (m, 1H), 1.89-1.84 (m, 3H), 1.73-1.67 (m, 1H), 1.52-1.25 (m, 10H), 1.17 (q, J=7.2 Hz, 3H), 0.88-0.85 (m, 3H), 0.79 (s, 3H); $^{13}$C NMR (CDCl$_3$/125 MHz): δ 150.1, 133.4, 129.2, 122.5, 44.2 (t, 1H), 30.3, 22.4, 15.9; HRMS (ESI): m/z calcd for C$_{12}$H$_{17}$OD [M–H]$^+$ 180.1493 found 180.1449.

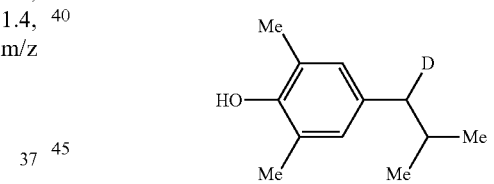

39-d1

Compound 40:

Isovalericaldehyde (82 µl, 0.75 mmol), Cu(OTf)$_2$ (2.2 mg, 2.5 mol %), ethanethiol (108 µl, 1.5 mmol) and 6-bromo-2-naphthol (55.75 mg, 0.25 mmol) were reacted according to method B. The mixture was stirred for 6 h at 50° C. After the addition of Et$_3$SiH (119 µl, 0.75 mmol) the reaction was stirred for 3 h at 50° C. The residual material was purified by column chromatography (silica gel 40-60, hexane/diethylether 95:5) affording compound 40 (57 mg, 78% yield) as a white solid. Characterization data of compound 40: $^1$H NMR (CDCl$_3$/400 MHz): δ 7.91 (d, J=1.8 Hz, 1H), 7.77 (d, J=9.1 Hz, 1H), 7.53 (dd, J=2, 9.2 Hz, 1H), 7.51 (d, J=9.2 Hz, 1H), 7.06 (d, J=8.9 Hz, 1H), 5.01 (br s, OH), 2.98 (m, 2H), 1.74 (hep, J=6.5 Hz, 1H), 1.53-1.47 (m, 2H), 1.03 (d, J=6.7 Hz, 6H); $^{13}$C NMR (CDCl$_3$/100 MHz): δ 150.5, 131.7, 130.7, 130.5, 129.5, 126.6, 124.9, 121.1, 118.7, 116.8, 38.9, 28.6, 23.1, 22.6; HRMS (ESI): m/z calcd for C$_{15}$H$_{17}$BrO [M–H]$^+$ 292.0457 and 294.0437, found 292.0457 and 294.0434.

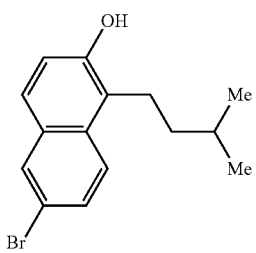

40

Compound 41:

Isobutylaldehyde (68 µl, 0.75 mmol), Cu(OTf)$_2$ (2.2 mg, 2.5 mol %), ethanethiol (108 µl, 1.5 mmol) and 2-naphthol (36 mg, 0.25 mmol) were reacted according to method B. The mixture was stirred for 6 h at 50° C. After the addition of Et$_3$SiH (116 µl, 0.75 mmol) the reaction was stirred for 2 h at 50° C. The residual material was purified by column chromatography (silica gel 40-60, hexane/ethyl acetate 96:4) affording compound 41 (44 mg, 87% yield) as a thick oil. Characterization data of compound 41: $^1$H NMR (CDCl$_3$/400 MHz): δ 7.96 (d, J=8.6 Hz, 1H), 7.8 (d, J=8.2 Hz, 1H), 7.66 (d, J=8.8 Hz, 1H), 7.51 (ddd, J=1.4, 6.4, 8.1, 1H), 7.36 (ddd, J=1.0, 6.8, 8.9 Hz, 1H), 7.09 (d, J=8.9 Hz, 1H), 5.01 (s, 1H), 2.96 (d, J=7.5 Hz, 2H), 2.18-2.08 (m, 1H), 1.06 (d, J=6.6 Hz, 6H); $^{13}$C NMR (CDCl$_3$/100 MHz): δ 150.9, 133.7, 129.5, 128.7, 127.8, 126.2, 123.5, 123.0, 119.4, 117.7, 34.1, 29.5, 22.8; HRMS (ESI): m/z calcd for C$_{14}$H$_{16}$O [M−H]$^+$ 199.1117, found 199.1116.

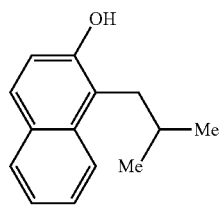

41

Compound 42:

Isobutyrlaldehyde (68 mg, 0.75 mmol), Cu(OTf)$_2$ (2.2 mg, 2.5 mol %), ethanethiol (108 µl, 1.5 mmol) and 6-methoxy-2-naphthol (43.5 mg, 0.25 mmol) were reacted according to method B. The mixture was stirred for 4 h at 50° C. in sealed tube. After the addition of Et$_3$SiH (116 µl, 0.75 mmol) the reaction was stirred for 4 h at 50° C. The residual material was purified by column chromatography (silica gel 40-60, hexane/ethyl acetate 95:5) affording compound 42 (45 mg, 78% yield) as a thick oil. Characterization data of compound 42: $^1$H NMR (CDCl$_3$/400 MHz): δ 7.82 (d, J=9.2 Hz, 1H), 7.52 (d, J=8.7 Hz, 1H), 7.15 (dd, J=2.7, 9.1 Hz, 1H), 7.10 (d, J=2.6 Hz, 1H), 7.05 (d, J=8.7 Hz, 1H), 4.74 (s, OH), 3.90 (s, 3H), 2.89 (d, J=7.2 Hz, 2H), 2.05 (h, J=6.9 Hz, 1H), 1.00 (d, J=6.6 Hz, 6H); $^{13}$C NMR (CDCl$_3$/100 MHz): δ 155.5, 149.4, 130.4, 128.9, 126.3, 125.1, 119.8, 118.7, 118.1, 106.8, 55.3, 34.2, 29.5, 22.8; HRMS (ESI): m/z calcd for C$_{15}$H$_{18}$O$_2$[M+H]$^+$ 229.1223, found 229.1223.

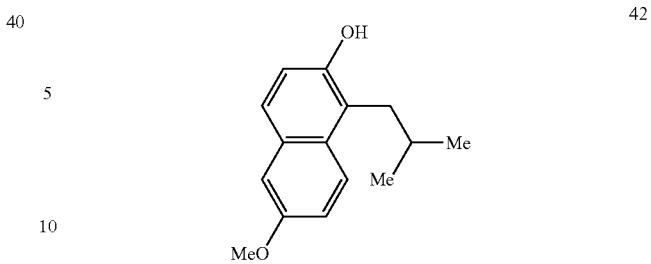

42

Compound 43:

Trimethylacetaldehyde (81 µl, 0.75 mmol), Cu(OTf)$_2$ (2.2 mg, 2.5 mol %), ethanethiol (108 µl, 1.5 mmol) and 3,5-dimethoxyphenol (38.5 mg, 0.25 mmol) were reacted according to method B. The mixture was stirred for 12 h at 50° C. After the addition of Et$_3$SiH (116 µl, 0.75 mmol) the reaction was stirred for 5 h at 50° C. The residual material was purified by column chromatography (silica gel 40-60, hexane/ethyl acetate 90:10) affording compound 43 (37 mg, 70% yield) as a white solid. Characterization data of compound 43: $^1$H NMR (CDCl$_3$/400 MHz): δ 6.10 (d, J=2.3, 1H), 6.06 (d, J=2.3 Hz, 1H), 4.94 (br s, OH), 3.76 (s, 3H), 3.74 (s, 3H), 2.49 (s, 2H), 0.94 (s, 9H); $^{13}$C NMR (CDCl$_3$/100 MHz): δ 159.9, 159.1, 155.6, 106.9, 93.2, 91.3, 55.2, 35.6, 33.5, 29.8; HRMS (ESI): m/z calcd for C$_{13}$H$_{20}$O$_3$ [M+H]$^+$ 225.1485, found 225.1503.

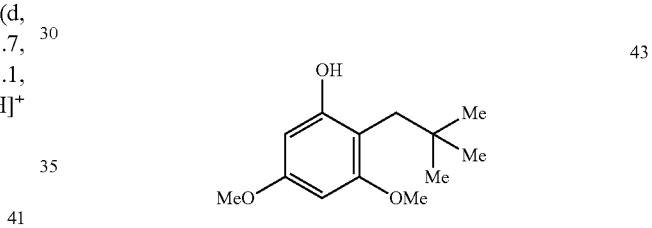

43

Compound 44:

Nonalaldehyde (129 µl, 0.75 mmol), Cu(OTf)$_2$ (2.2 mg, 2.5 mol %), ethanethiol (108 µl, 1.5 mmol) and 3,4,5-trimethoxyphenol (46 mg, 0.25 mmol) were reacted according to method B. The mixture was stirred for 7 h at 50° C. After the addition of Et$_3$SiH (116 µl, 0.75 mmol) the reaction was stirred for 4 h at 50° C. The residual material was purified by column chromatography (silica gel 40-60, hexane/ethyl acetate 85:15) affording compound 44 (48 mg, 62% yield) as a thick oil. Characterization data of compound 44: $^1$H NMR (CDCl$_3$/400 MHz): δ 6.19 (s, 1H), 3.87 (s, 3H), 3.80 (s, 3H), 3.75 (s, 3H), 2.52 (t, J=7.9 Hz, 2H), 1.53-1.45 (m, 2H), 1.35-1.20 (m, 12H), 0.87 (t, J=7.0 Hz, 3H); $^{13}$C NMR (CDCl$_3$/100 MHz): δ 152.4, 151.5, 149.8, 136.1, 114.6, 96.0, 61.2, 61.0, 55.9, 31.9, 30.2, 29.9, 29.6, 29.6, 29.4, 23.7, 22.7, 14.1; HRMS (ESI): m/z calcd for C$_{18}$H$_{30}$O$_4$ [M+H]$^+$ 311.2217, found 311.2213.

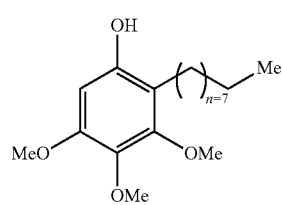

44

Compound 45:

4-chlorobenzaldehyde (130.5 mg, 0.75 mmol), Cu(OTf)$_2$ (2.2 mg, 2.5 mol %), ethanethiol (108 μl, 1.5 mmol) and sesamol (34.5 mg, 0.25 mmol) were reacted according to method B. The mixture was stirred for 4 h at 50° C. After the addition of Et$_3$SiH (116 μl, 0.75 mmol) the reaction was stirred for 3 h at 50° C. The residual material was purified by column chromatography (silica gel 40-60, hexane/ethyl acetate 90:10) affording compound 45 (60 mg, 91% yield) as a thick oil. Characterization data of compound 45: $^1$H NMR (CDCl$_3$/400 MHz): δ 7.26-7.23 (m, 2H), 7.15-7.12 (m, 2H), 6.56 (s, 1H), 6.39 (s, 1H), 5.88 (s, 2H), 3.85 (s, 2H); $^{13}$C NMR (CDCl$_3$/100 MHz): δ 147.9, 146.7, 141.6, 138.8, 132.0, 129.9, 118.6, 110.0, 101.1, 98.6, 35.3; HRMS (ESI): m/z calcd for C$_{14}$H$_{11}$ClO$_3$ [M+H]$^+$ 263.0469, found 263.0474.

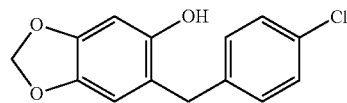

45

Compound 46:

7-hyroxycitronellal (140 μl, 0.75 mmol), Cu(OTf)$_2$ (2.2 mg, 2.5 mol %), ethanethiol (108 μl, 1.5 mmol) and 1,3,5-trimethoxybenzene (42 mg, 0.25 mmol) were reacted according to method B. The mixture was stirred for 2 h at rt. After the addition of Et$_3$SiH (116 μl, 0.75 mmol) the reaction was stirred for 1 h at room temperature. The residual material was purified by column chromatography (silica gel 40-60, hexane/ethyl acetate 80:20) affording compound 46 (64 mg, 79% yield) as a thick oil. Characterization data of compound 46: $^1$H NMR (CDCl$_3$/400 MHz): δ 6.13 (s, 2H), 3.80 (s, 3H), 6.79 (s, 6H), 2.60-2.48 (m, 2H), 1.49-1.24 (m, 9H), 1.21 (s, 6H), 0.93 (d, J=6.2, Hz, 3H); $^{13}$C NMR (CDCl$_3$/100 MHz): δ 159.0, 158.7, 112.3, 90.6, 71.1, 55.7, 55.3, 44.4, 37.3, 36.6, 32.9, 29.3, 29.2, 21.6, 20.1, 19.7; HRMS (ESI): m/z calcd for C$_{19}$H$_{32}$O$_4$[M+H]$^+$ 325.2373 found 325.2363.

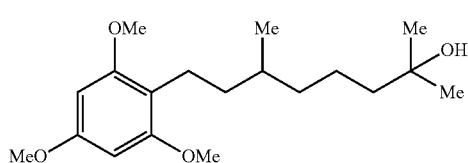

46

Compound 47:

3-((7-chloro-3,7 dimethyloctyl)oxy)benzaldehyde (87 mg, 0.29 mmol), Cu(OTf)$_2$ (2.2 mg, 2.5 mol %), ethanethiol (43 μl, 0.6 mmol) and 1,3,5-trimethoxybenzne (33.6 mg, 0.2 mmol) were reacted according to method B. The mixture was stirred for 0.5 h at 50° C. After the addition of Et$_3$SiH (119 μl, 0.75 mmol) the reaction was stirred for 4 h at 50° C. The residual material was purified by column chromatography (silica gel 40-60, hexane/ethyl acetate 95:5) affording compound 47 (81 mg, 90% yield) as a thick oil. Characterization data of compound 47: $^1$H NMR (CDCl$_3$/400 MHz): δ 7.13 (t, J=8.0 Hz, 1H), 6.82 (m, 2H), 6.68 (d, J=8.0 Hz, 1H), 6.17 (s, 2H), 3.97 (q, J=6.4 Hz, 2H), 3.93 (s, 2H), 3.82 (s, 3H), 3.80 (s, 6H), 1.87-1.79 (m, 1H), 1.76-1.68 (m, 2H), 1.59 (s, 6H), 1.56-1.51 (m, 2H), 1.43-1.35 (m, 1H), 1.27-1.18 (m, 2H), 0.97 (d, J=6.3 Hz, 3H); $^{13}$C NMR (CDCl$_3$/100 MHz): δ 159.7, 158.9, 143.9, 128.8, 120.8, 114.9, 111.3, 110.1, 90.7, 71.3, 65.9, 55.7, 55.4, 46.3, 37.1, 36.3, 32.5, 29.8, 28.9, 28.4, 22.5, 19.6; HRMS (ESI): m/z calcd for C$_{26}$H$_{37}$ClO$_4$ [M+H]$^+$ 449.2453 found 449.2449.

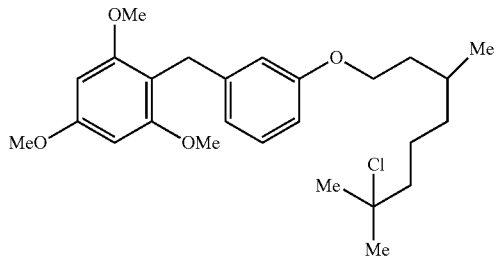

47

Compound 48:

Prepared according to method B with 3-(allyloxy)benzaldehyde (81 mg, 0.5 mmol), Cu(OTf)$_2$ (2.2 mg, 2.5 mol %), ethanethiol (72 μl, 1.0 mmol) and 1,3,5-trimethoxybenzene (42 mg, 0.25 mmol). The mixture was stirred for 1.5 h at rt. After the addition of Et$_3$SiH (116 μl, 0.75 mmol) the reaction was stirred at room temperature for 0.5 h. The residual material was purified by column chromatography (silica gel 40-60, hexane/ethyl acetate 93:7) to obtain compound 48 (74 mg, 94% yield) as a thick oil. Characterization data of compound 48: $^1$H NMR (CDCl$_3$/400 MHz): δ 7.12 (d, J=7.8 Hz, 1H), 6.84 (d, J=7.8 Hz, 1H), 6.82 (s, 1H), 6.68 (dd, J=8.3, 1.8 Hz, 2H), 6.15 (s, 2H), 6.05 (ddt, J=17.0, 10.7, 5.2, 1H), 5.39 (dd, J=17.0, 1.2 Hz, 1H), 5.39 (dd, J=10.5, 0.7 Hz, 1H), 4.49 (d, J=10.5, 5.2, 2H), 3.91 (s, 2H), 3.81 (s, 3H), 3.79 (s, 6H); $^{13}$C NMR (CDCl$_3$/100 MHz): δ 159.7, 158.9, 158.5, 144.0, 133.7, 128.8, 121.2, 117.5, 115.1, 111.3, 110.0, 90.6, 68.7, 55.7, 55.4, 28.3; HRMS (ESI): m/z calcd for C$_{19}$H$_{22}$O$_4$[M+H]$^+$ 337.1410 found 337.1406.

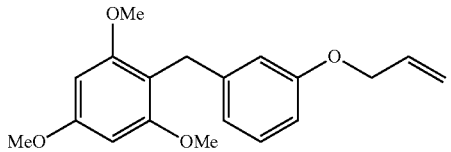

48

Compound 49a:

4-cyanobenzaldehyde (98 mg, 0.75 mmol), Cu(OTf)$_2$ (2.2 mg, 2.5 mol %), ethanethiol (108 μl, 1.5 mmol) and 1,3,5-trimethoxybenzene (42 mg, 0.25 mmol) were reacted according to method B. The mixture was stirred at 50° C. for 3 h. After the addition of Et$_3$SiH (116 μl, 0.75 mmol) the reaction was stirred for 2 h at 50° C. The residual material was purified by column chromatography (silica gel 40-60, hexane/ethyl acetate 90:10) affording compound 49a (69 mg, 97% yield) as a white solid. Characterization data of compound 49a: $^1$H NMR (CDCl$_3$/400 MHz): δ 7.48 (d, J=8.4 Hz, 2H), 7.31 (d, J=8.3 Hz, 2H), 6.15 (s, 2H), 3.96 (s, 2H), 3.81 (s, 3H), 3.78 (s, 3H); $^{13}$C NMR (CDCl$_3$/100 MHz): δ 160.2, 158.8, 148.2, 131.8, 129.2, 119.5, 108.9, 108.5, 90.6, 55.7, 55.4, 28.7.

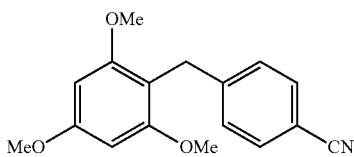

49a

Compound 49:

Isobutyraldehyde (97 µl, 1.06 mmol), Cu(OTf)$_2$ (3.2 mg, 2.5 mol %), ethanethiol (153 µl, 2.12 mmol) and 4-(2,4,6-trimethoxybenzyl)benzonitrile (100 mg, 0.35 mmol) were reacted according to method B. The mixture was stirred for 10 h at 50° C. After the addition of Et$_3$SiH (116 µl, 0.75 mmol) the reaction was stirred for 4 h at 50° C. The residual material was purified by column chromatography (silica gel 40-60, hexane/ethyl acetate 93:7) affording compound 49 (51 mg, 43% yield) as a thick oil. Characterization data of compound 49: $^1$H NMR (CDCl$_3$/400 MHz): δ 7.49 (d, J=8.1 Hz, 2H), 7.27 (d, J=8.1 Hz, 2H), 6.31 (s, 1H), 4.01 (s, 2H), 3.82 (s, 3H), 3.76 (s, 3H), 3.58 (s, 3H), 2.46 (d, J=7.3 Hz, 2H), 1.89 (non, J=6.7 Hz, 1H), 0.87 (d, J=6.7 Hz, 6H); $^{13}$C NMR (CDCl$_3$/100 MHz): δ 158.5, 158.2, 156.8, 148.2, 131.9, 129.0, 119.4, 116.0, 112.8, 109.1, 91.7, 61.5, 55.6, 55.5, 32.6, 29.7, 28.8, 22.6; HRMS (ESI): m/z calcd for C$_{21}$H$_{25}$NO$_3$ [M+Na]$^+$ 340.1907 found 340.1900.

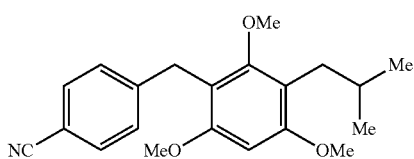

49

Compound 50:

Benzaldehyde (77 µl, 0.75 mmol), Cu(OTf)$_2$ (2.2 mg, 2.5 mol %), ethanethiol (108 µl, 1.5 mmol) and β-estradiol (68 mg, 0.25 mmol) were reacted according to method B. The mixture was stirred for 8 h at 50° C. After the addition of Et$_3$SiH (116 µl, 0.75 mmol) the reaction was stirred for 4 h at 50° C. The residual material was purified by column chromatography (silica gel 40-60, hexane/ethyl acetate 85:15) affording compound 50 (77 mg, 85% yield) as a thick oil. Characterization data of compound 50: $^1$H NMR (CDCl$_3$/500 MHz): δ 7.31-7.18 (m, 5H), 7.05 (s, 1H), 6.52 (s, 1H), 4.00-3.91 (m, 2H), 3.73 (t, J=8.4 Hz, 1H), 2.85-2.74 (m, 2H), 2.28-2.24 (m, 1H), 2.20-2.07 (m, 2H), 1.96-1.82 (m, 2H), 1.73-1.66 (m, 1H), 1.52-1.15 (m, 7H), 0.78 (s, 3H); $^{13}$C NMR (CDCl$_3$/100 MHz): δ 151.6, 140.4, 136.4, 132.7, 130.1, 128.6, 128.6, 128.0, 128.0, 126.2, 124.2, 115.8, 82.0, 50.0, 44.0, 43.3, 38.9, 36.7, 36.4, 30.6, 29.3, 27.3, 26.4, 23.2, 11.3; [α]$_D^{22.8}$: +54.5 (c=0.55, CHCl$_3$); HRMS (ESI): m/z calcd for C$_{25}$H$_{30}$O$_2$[M+Na]$^+$ 385.2138 found 385.2137.

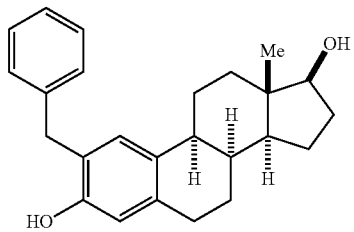

50

Compound 51:

Isobutyraldehyde (68 µl, 0.75 mmol), Cu(OTf)$_2$ (2.2 mg, 2.5 mol %), ethanethiol (108 µl, 1.5 mmol) and β-estradiol (68 mg, 0.25 mmol) were reacted according to method B. The mixture was stirred for 8 h at 50° C. After the addition of Et$_3$SiH (116 µl, 0.75 mmol) the reaction was stirred for 4 h at 50° C. The residual material was purified by column chromatography (silica gel 40-60, hexane/ethyl acetate 80:20) affording compound 51 (55 mg, 67% yield) as a with solid. Characterization data of compound 51: $^1$H NMR (CDCl$_3$/400 MHz): δ 6.98 (s, 1H), 6.49 (s, 1H), 4.54 (s, 1H), 3.74 (t, J=8.5 Hz, 1H), 2.86-2.75 (m, 2H), 2.45-2.40 (m, 2H), 2.35-2.29 (m, 1H), 2.20-2.08 (m, 2H), 1.97-1.83 (m, 3H), 1.74-1.66 (m, 1H), 1.53-1.28 (m, 7H), 1.23-1.15 (m, 1H), 0.93 (d, J=6.6 Hz 6H), 0.78 (s, 3H); $^{13}$C NMR (CDCl$_3$/100 MHz): δ 151.4, 135.5, 132.3, 128.2, 124.7, 115.2, 82.0, 50.1, 44.0, 43.3, 39.3, 38.9, 36.8, 30.6, 29.2, 29.1, 27.3, 26.4, 23.2, 22.7, 11.1; [α]$_D^{22.8}$: +70.8 (c=0.57, CHCl$_3$); HRMS (ESI): m/z calcd for C$_{25}$H$_{30}$O$_2$[M+H]$^+$ 363.2319 found 363.2318.

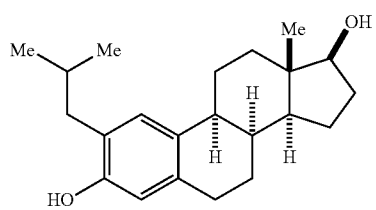

51

Compound 52:

Benzaldehyde (25.5 µl, 0.25 mmol), Cu(OTf)$_2$ (2.2 mg, 2.5 mol %), ethanethiol (21.6 µl, 0.3 mmol, 1.2 equiv) and 1,3,5-trimethoxybenene (68 mg, 0.25 mmol). The mixture was stirred for 4 h at 50° C. After the addition of Et$_3$SiH (116 µl, 0.75 mmol) the reaction was stirred for 2 h at 50° C. The residual material was purified by column chromatography (silica gel 40-60, hexane/ethyl acetate 95:5) affording compound 52 (52 mg, 80% yield) as a thick oil. Characterization data of compound 52: $^1$H NMR (CDCl$_3$/500 MHz): δ 7.17-7.10 (m, 4H), 7.04-7.01 (m, 1H), 6.07 (s, 2H), 3.85 (s, 2H), 3.72 (s, 3H), 3.70 (s, 3H); $^{13}$C NMR (CDCl$_3$/100 MHz): δ 159.7, 158.9, 142.3, 128.4, 128.0, 125.3, 110.3, 90.6, 55.7, 55.3, 28.3; HRMS (ESI): m/z calcd for C$_{16}$H$_{18}$O$_3$ [M+H]$^+$ 259.1329 found 259.1328.

52

Compound 53:

To a stirred solution of compound 23 (284 mg, 1 mmol) in 2,2,2-trifluoroethanol (2 ml) was added H$_2$O$_2$ (102 µl, 30% in H$_2$O, 1 mmol) at 0° C. The mixture was stirred for 1 h, all volatiles were removed under reduced pressure and the residual crude material was purified by column chromatography (silica gel 40-60, ethyl acetate) affording compound 53 (240 mg, 80% yield) as a thick oil. Characterization data of compound 53: $^1$H NMR (CDCl$_3$/400 MHz): δ 6.12 (s, 1H), 6.10 (s, 1H), 4.01 (d, J=10.7 Hz, 1H), 3.76 (s, 3H), 3.75 (s, 3H), 3.73 (s, 3H), 2.93-2.83 (m, 1H), 2.61-2.54 (m, 1H), 2.47-2.40 (m, 1H), 1.25 (t, J=7.5 Hz, 3H), 1.09 (d, J=6.6 Hz, 3H), 0.75 (d, J=6.6 Hz, 3H); $^{13}$C NMR (CDCl$_3$/100 MHz): δ 160.9, 160.8, 159.6, 103.2, 91.4, 90.7, 65.1, 55.9, 55.7, 55.2, 45.6, 28.0, 25.4, 22.4, 21.9, 7.8; HRMS (ESI): m/z calcd for C$_{15}$H$_{24}$O$_4$S [M+Na]$^+$ 323.1288 found 323.1285.

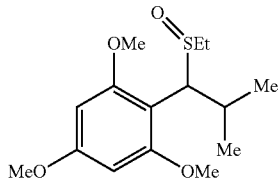

53

One-Pot Follow-Up Procedure to Compound 53:

Isobutyrlaldehyde (68 μl, 0.75 mmol), Cu(OTf)$_2$ (2.2 mg, 2.5 mol %), ethanethiol (108 μl, 1.5 mmol) and 1,3,5-trimethoxybenzene (42 mg, 0.25 mmol) were reacted according to method A. The mixture was stirred in sealed tube at 50° C. for 2 h. Then the mixture was cooled to 0° C., H$_2$O$_2$ (51 μl, 30% in H$_2$O, 0.5 mmol) was added slowly. And the reaction was further stirred for 1 h. After removal of all volatiles under reduced pressure, the residual crude material was purified by column chromatography (silica gel 40-60, ethyl acetate) affording compound 53 (41 mg, 55% yield) as a thick oil.

Compound 54:

A solution of sulfoxide 53 (60 mg, 0.2 mmol), allyltrimethylsilane (95 ml, 0.6 mmol) and Cu(OTf)$_2$ (1.8 mg, 2.5 mol %) in 2,2,2-trifluoroethanol (0.4 ml) were stirred at room temperature for 2 h. After completion of the reaction, as indicated by TLC analysis, all volatiles were removed under reduced pressure and the residual crude material was purified by column chromatography (silica gel 40-60, ethyl acetate/hexane 97:3) affording compound 54 (41 mg, 78% yield) as a thick oil. Characterization data of compound 54: $^1$H NMR (CDCl$_3$/400 MHz): δ 6.11 (s, 2H), 5.61-5.51 (m, 1H), 4.84 (d, J=17.0 Hz, 1H), 4.73 (d, J=10.0 Hz, 1H), 3.80 (s, 3H), 3.75 (s, 6H), 2.95 (dt, J=5.4, 4.9 Hz, 1H), 2.62-2.54 (m, 1H), 2.48-2.42 (m, 1H), 2.16-2.07 (m, 1H), 1.01 (d, J=6.6 Hz, 3H), 0.75 (d, J=6.7 Hz, 3H); $^{13}$C NMR (CDCl$_3$/100 MHz): δ 159.7, 158.9, 139.5, 113.7, 113.4, 91.2, 90.7, 56.1, 55.1, 42.4, 35.7, 30.8, 21.9; HRMS (ESI): m/z calcd for C$_{16}$H$_{24}$O$_3$[M+Na]$^+$ 265.1798 found 265.1797.

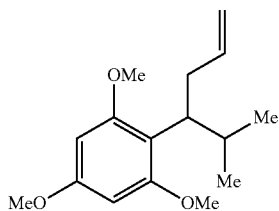

54

Compound 3a:

To a stirred solution of compound 3 (284 mg, 1 mmol) in 2,2,2-trifluoroethanol (2 ml) was added H$_2$O$_2$ (102 μl, 30% in H$_2$O, 1 mmol) at 0° C. The mixture was stirred for 1 h, all volatiles were removed under reduced pressure and the residual crude material was purified by column chromatography (silica gel 40-60, ethyl acetate) affording compound 3a (72 mg, 94% yield) as a thick oil. Characterization data of compound 3a: $^1$H NMR (CDCl$_3$/500 MHz): δ 7.39-7.38 (m, 2H), 7.32-7.30 (m, 2H), 6.92-6.88 (m, 4H), 4.73 (s, 1H), 3.79 (s, 3H), 3.77 (s, 3H), 2.57-2.49 (m, 1H), 2.46-2.39 (m, 1H), 1.27 (t, J=7.5 Hz, 3H); $^{13}$C NMR (CDCl$_3$/125 MHz): δ 159.1, 159.4, 130.4, 129.7, 128.1, 127.4, 114.6, 114.2, 70.3, 55.3, 55.3, 44.1; HRMS (ESI): m/z calcd for C$_{17}$H$_{20}$O$_3$S [M+Na]$^+$ 327.1025 found 327.1025.

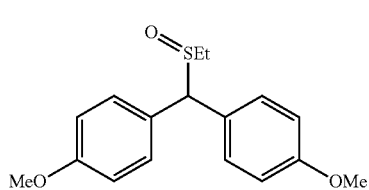

3a

Compound 55:

A solution of compound 3a (131 mg, 0.43 mmol) was treated with 1,3,5-trimethoxybenzene (145 ml, 0.86 mmol) at rt in trifuloroethanol (0.8 ml), followed by addition of Cu(OTf)$_2$ (4 mg, 2.5 mol %). The mixture was stirred for 0.5 h at rt. The residual material was purified by column chromatography (silica gel 40-60, hexane/ethyl acetate 93:7) affording compound 55 (151 mg, 89% yield) as a thick pink oil. Characterization data of compound 55: $^1$H NMR (CDCl$_3$/500 MHz): δ 7.14 (d, J=8.1 Hz, 4H), 6.80 (d, J=8.7 Hz, 4H), 6.18 (s, 2H), 5.99 (s, 1H), 3.82 (s, 3H), 3.80 (s, 6H), 3.63 (s, 6H); $^{13}$C NMR (CDCl$_3$/125 MHz): δ 159.9, 159.1, 157.4, 136.6, 130.0, 114.1, 113.0, 91.7, 55.8, 55.3, 55.2, 43.6; HRMS (ESI): m/z calcd for C$_{24}$H$_{26}$O$_5$[M+Na]$^+$ 395.1853 found 395.1853.

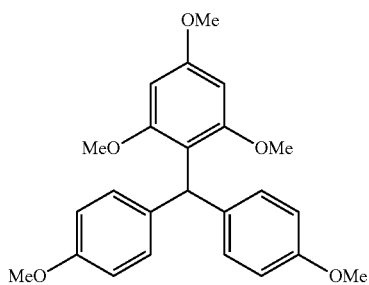

55

Compound 56:

A solution of compound 3a (76 mg, 0.25 mmol), azidotrimethylsilane (130 ml, 1 mmol) and Cu(OTf)$_2$ (2.2 mg, 2.5 mol %) in 2,2,2-trifluoroethanol (0.75 ml) was stirred at room temperature for 1.5 h. The residual crude material was purified by column chromatography (silica gel 40-60, hexane/ethyl acetate 95:5) to obtain compound 56 (59 mg, 87% yield) as a thick colorless oil. Characterization data of compound 56: $^1$H NMR (CDCl$_3$/400 MHz): δ 7.23 (d, J=8.5 Hz, 4H), 6.90 (d, J=8.5 Hz, 4H), 5.65 (s, 1H), 3.81 (s, 6H); $^{13}$C NMR (CDCl$_3$/100 MHz): δ 159.3, 132.1, 128.6, 114.0, 67.7, 55.3; HRMS (ESI): m/z calcd for C$_{15}$H$_{15}$N$_3$O$_2$ [M+Na]$^+$ 292.1056 found 292.1055.

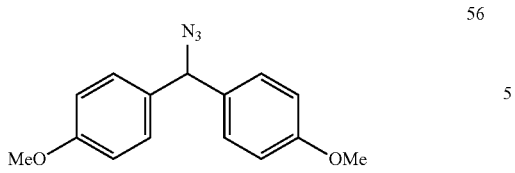

56

Example 3

Exploring the Role of the Thiol in the Synthesis Route

General:

Scheme 2 presents exemplary electrophilic aromatic substitution of aldehydes and thionium ions following mixing 2-naphthol (1a in scheme 2) with an excess of isobutyraldehyde (2a in scheme 2) under acid-catalyzed conditions (Cu(OTf)$_2$ (5 mol %), 2,2,2-trifluoroethanol, room temperature) produced a complex reaction mixture, with naphthofurans being the major products (28% and 14% yields, respectively):

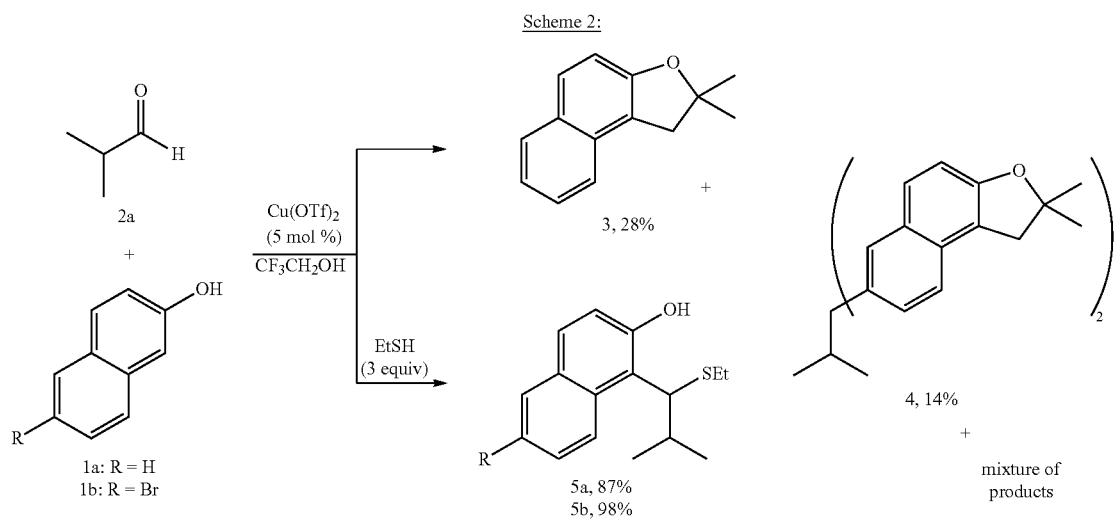

Scheme 2:

In exemplary procedure, a solution of isobutylaldehyde (68 μl, 0.75 mmol) was treated with Cu(OTf)$_2$ (2.2 mg, 2.5 mol %) at rt in trifuloroethanol (0.75 ml), followed by addition of 2-naphthol (36 mg, 0.25 mmol). The mixture was stirred for 10 h at 60° C. The residual material was purified by column chromatography (silica gel 40-60, hexane/ether 98:2) to obtain compound 3 in scheme 2 (also referred to as "RP_984") (13.7 mg, 28% yield) as white solid.

Compound A1' and A2':

Characterization data of compound 3 (referred to as: "A1'''"): $^1$H NMR (CDCl$_3$/400 MHz): δ 7.80 (d, J=8.1 Hz, 1H), 7.68 (d, J=8.7 Hz, 1H), 7.55 (d, J=8.2 Hz, 1H), 7.46 (t, J=7.5 Hz, 1H), 7.29 (t, J=7.5 Hz, 1H), 7.08 (d, J=8.7 Hz, 1H), 3.29 (s, 2H), 1.57 (s, 6H); $^{13}$C NMR (CDCl$_3$/100 MHz): δ 156.2, 131.2, 129.0, 128.9, 128.7, 126.6, 122.6, 122.6, 118.2, 112.4, 87.5, 41.8, 28.6; HRMS (ESI): m/z calcd for C$_{14}$H$_{14}$O [M+H]$^+$ 199.1117, found 199.1115.

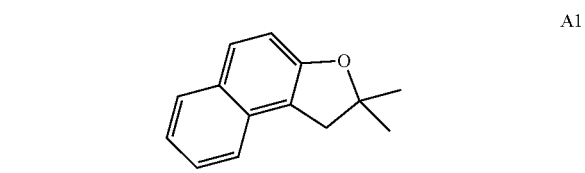

A1

Control Experiment—The Disassemble of Ethyl(phenyl(2,4,6-trimethoxyphenyl)methyl)sulfane 6 to Dithioacetal 6a and 1,3,5-trimethoxybenzene 1d.

Procedure:

A solution of compound 6 as described hereinbelow (40 mg, 0.125 mmol), ethanethiol (18 μl, 0.25 mmol) and Cu(OTf)$_2$ (1.1 mg, 2.5 mol %) in 2,2,2-trifluoroethanol (0.375 ml) was stirred for 16 h at 50° C. The process is shown in Scheme 2a below.

Scheme 2a:

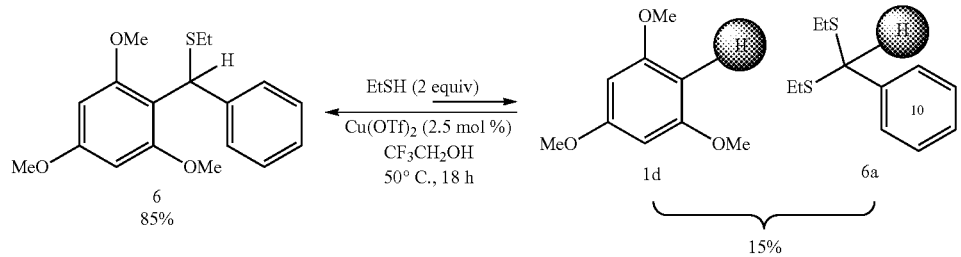

Characterization data of compound 4 (referred to as "A2'"): $^1$H NMR (CDCl$_3$/400 MHz): δ 7.73 (s, 2H), 7.63 (d, J=8.8 Hz, 2H), 7.44 (s, 4H), 7.02 (d, J=8.8 Hz, 2H), 3.69 (d, J=10.7 Hz, 1H), 3.21 (s, 4H), 2.75-2.65 (m, 1H), 1.53 (s, 6H), 1.52 (s, 6H), 0.97 (d, J=6.4 Hz, 6H); $^{13}$C NMR (CDCl$_3$/100 MHz): δ 155.8, 139.1, 129.7, 129.2, 128.6, 127.5, 127.2, 122.8, 118.1, 112.3, 87.4, 60.5, 41.8, 31.4, 28.6, 22.0; HRMS (ESI): m/z calcd for C$_{32}$H$_{34}$O$_2$[M+H]$^+$ 451.2636, found 451.2636.

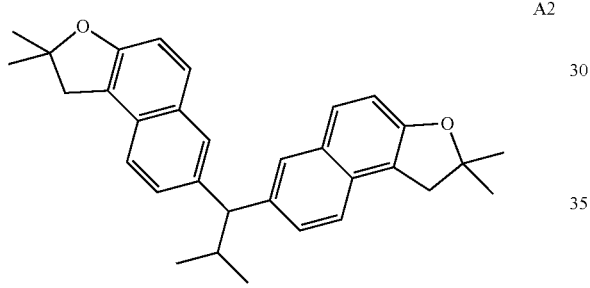

A2

This picture changed completely when the reaction was performed in the presence of ethanethiol (e.g., 3 equiv), leading to a Pummerer type reaction: as demonstrated in scheme 2, the isobuyraldehyde is protected as a dithioacetal that transforms under the acidic conditions to an active thionium ion species that reacts with naphthols (designated as "1a" or "1b" in Scheme 2), affording benzylsulfides (5a and 5b in Scheme 2) in 87% and 98% isolated yields, respectively.

Example 4

Synthesis Summary with Various Primary Alkyl Groups

The generality of the disclosed alkylation protocol was examined and the results are described hereinbelow.

The method enables a direct entry to both linear and branched primary alkyl substituents. Alkyl groups such as methyl (product B1, 51% yield), ethyl (B2, 81%), isobutyl (B3, 73% and B4, 78%), isopentyl (B5, 87% and B6, 78%) neopentyl (B7, 70%) and octanyl (B8, 63%) were installed in high chemo- and regioselectivity. Importantly, functional groups that are incompatible with the Friedel-Crafts reaction or are sensitive toward reduction, such as primary alkyl bromide (B9, 62%), tertiary alkyl chloride (B10, 90%), tertiary alcohols (B11, B12; 85%, 42%, respectively) and aromatic nitrile (B13, 70%) were not affected. Finally, an isotope labeled alkyl group can be introduced by using Et$_3$SiD as the reducing agent, affording B3-d$_1$ in 71%. B13 refers to two-step synthesis: the first is benzylation and the second is alkylation.

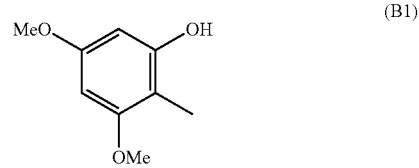
(B1)

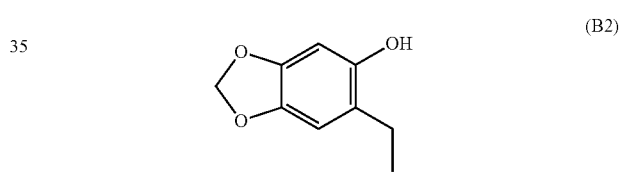
(B2)

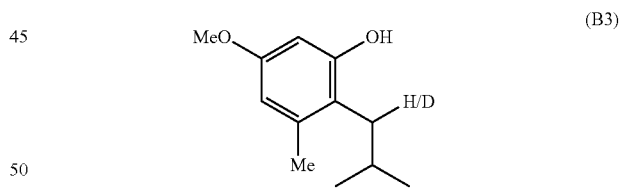
(B3)

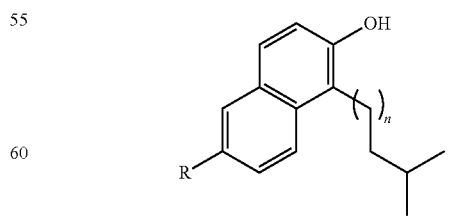

B4 n = 0, R = Br, 78%
B5: n = 0, R = H, 87%
B6: n = 1, R = OMe, 78%

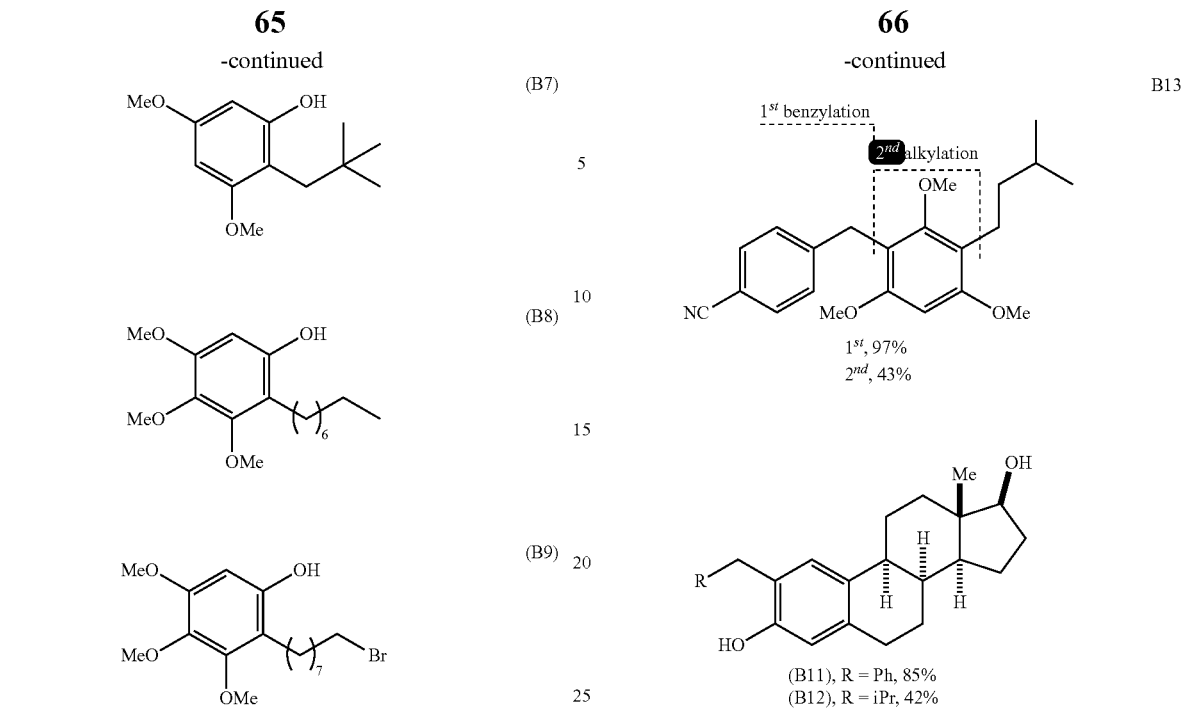

Example 5

The Reaction in Aqueous Solutions

Contrary to the classic Friedel-Crafts alkylation, which requires anhydrous conditions, the electrophilic aromatic substitution as disclosed herein can be carried out in water, as exemplified for the coupling of glutaraldehyde (scheme 3, 2b, 25% v/v in H$_2$O), which probably transforms to thionium ion (designated as "I") before reacting with arene (designated as "1c") to afford dithioacetal 32 in moderate 58% yield (Scheme 3).

Scheme 3:

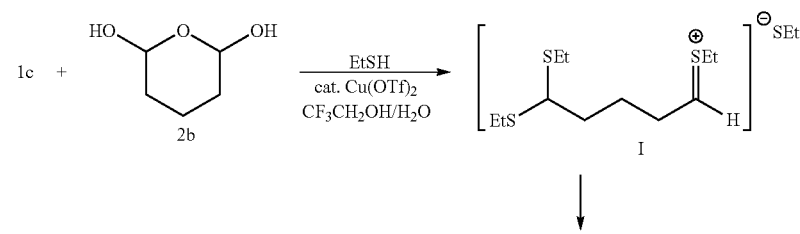

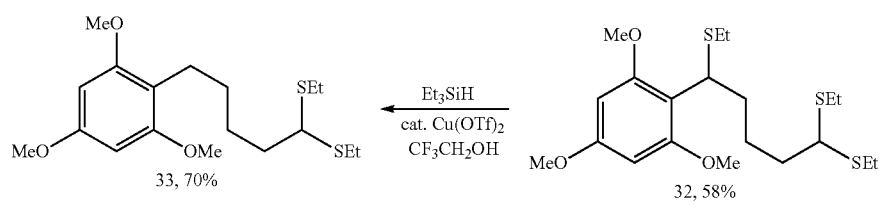

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A process comprising:
reacting a compound having Formula II:

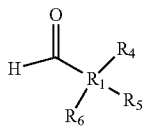

with a compound having Formula III:

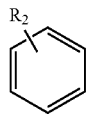

and with $R_3SH$
in the presence of an acidic catalyst and a suitable solvent, thereby forming a compound having Formula I:

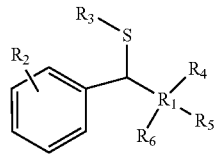

wherein:
$R_1$ is $(C)_n$ or aryl, wherein n is between 1 to 20;
$R_2$ represents 0 to 5 substituents, wherein, in each occurrence, each substituent is independently selected from the group consisting of: alkyl, alkenyl, alkynyl, cycloalkyl, heteroalicyclic, aryl, heteroaryl, hydroxy, alkoxy, aryloxy, thiohydroxy, thioalkoxy, thioaryloxy, halide, amine, amide, carbonyl, thiocarbonyl, carboxy, thiocarboxy, epoxide, sulfonate, sulfonyl, sulfinyl, sulfonamide, nitro, nitrile, isonitrile, thiirane, aziridine, nitroso, hydrazine, sulfate, azide, phosphonyl, phosphinyl, urea, thiourea, carbamyl and thiocarbamyl, or the substituents are joined together so as to form a fused ring system containing up to three 6-member carbocyclic, each being substituted or non-substituted;

$R_3$ is selected from alkyl, aryl, alkoxy, aryloxy, carbonyl, carboxy, substituted or non-substituted; and $R_4$, $R_5$, and $R_6$ are each independently selected from the group consisting of: hydrogen, alkyl, alkenyl, alkynyl, cycloalkyl, heteroalicyclic, aryl, heteroaryl, hydroxy, alkoxy, aryloxy, thiohydroxy, thioalkoxy, thioaryloxy, halide, amine, amide, carbonyl, thiocarbonyl, carboxy, thiocarboxy, epoxide, sulfonate, sulfonyl, sulfinyl, sulfonamide, nitro, nitrile, isonitrile, thiirane, aziridine, nitroso, hydrazine, sulfate, azide, phosphonyl, phosphinyl, urea, thiourea, carbamyl and thiocarbamyl, the process further comprising a subsequent step of reacting said compound having Formula I with a reducing agent, thereby forming the compound having Formula IV:

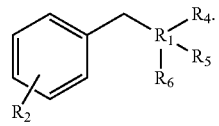

2. The process of claim 1, wherein $R_3$ is ethyl.

3. The process of claim 1, wherein said acidic catalyst is one or more Lewis acid selected from the group consisting of: $CuCl_2$, $Sc(OTf)_3$, $Fe(OTf)_3$, $In(OTf)_3$, $BF3.OEt_2$, and $Cu(OTf)_2$.

4. The process of claim 1, wherein said acidic catalyst is one or more Brønsted acids selected from the group consisting of: Triflic acid (TfOH), para-toluenesulfonic acid, and trifluoroacetic acid.

5. The process of claim 1, wherein said suitable solvent is a polar solvent selected from the group consisting of: acetonitrile, nitromethane, and 2,2,2-trifluoroethanol (TFE), hexafluoroisopropanol (HFIP) or a mixture thereof.

6. The process of claim 1, characterized by at least 30% yield of the compound having Formula I.

7. The process of claim 1, wherein said reducing agent is a silane.

8. The process of claim 7, wherein said silane is $Et_3SiH$.

* * * * *